(12) United States Patent
Kondoh et al.

(10) Patent No.: US 7,794,907 B2
(45) Date of Patent: Sep. 14, 2010

(54) HYDRAZONE COMPOUND, ELECTROPHOTOGRAPHIC PHOTORECEPTOR COMPRISING THE HYDRAZONE COMPOUND, AND IMAGE FORMING APPARATUS EQUIPPED WITH THE ELECTROPHOTOGRAPHIC PHOTORECEPTOR

(75) Inventors: Akihiro Kondoh, Nara (JP); Takatsugu Obata, Nara (JP)

(73) Assignee: Sharp Kabushiki Kaisha, Osaka (JP)

( * ) Notice: Subject to any disclaimer, the term of this patent is extended or adjusted under 35 U.S.C. 154(b) by 704 days.

(21) Appl. No.: 11/220,401

(22) Filed: Sep. 7, 2005

(65) Prior Publication Data
US 2006/0057481 A1 Mar. 16, 2006

(30) Foreign Application Priority Data
Sep. 7, 2004 (JP) .......................... P2004-259877

(51) Int. Cl.
G03G 5/05 (2006.01)
(52) U.S. Cl. ............................. 430/70; 430/72; 430/75; 430/76; 546/332; 564/251; 564/250
(58) Field of Classification Search .................... 430/70, 430/72, 75, 79; 546/332; 564/251, 250
See application file for complete search history.

(56) References Cited

U.S. PATENT DOCUMENTS

| | | | |
|---|---|---|---|
| 3,824,099 A | 7/1974 | Champ et al. | |
| 4,123,269 A | 10/1978 | Von Hoene et al. | |
| 4,150,987 A | 4/1979 | Anderson et al. | |
| 4,278,747 A | 7/1981 | Murayama et al. | |
| 4,338,388 A | 7/1982 | Sakai et al. | |
| 4,367,273 A | 1/1983 | Murayama et al. | |
| 4,396,694 A * | 8/1983 | Nagata et al. | 430/58.4 |
| 4,859,556 A | 8/1989 | Sasaki | |
| 4,892,949 A | 1/1990 | Sasaki | |
| 2004/0101770 A1* | 5/2004 | Obata et al. | 430/58.85 |
| 2006/0276433 A1* | 12/2006 | Kawagoe et al. | 514/63 |

FOREIGN PATENT DOCUMENTS

| | | |
|---|---|---|
| JP | 52-4188 | 2/1977 |
| JP | 54-150128 | 11/1979 |
| JP | 54-151955 | 11/1979 |
| JP | 55-52063 | 4/1980 |
| JP | 55-42380 | 10/1980 |
| JP | 58-32372 | 7/1983 |

(Continued)

OTHER PUBLICATIONS

English translation of JP 2001305754, Inagaki et al., Feb. 2001.*

*Primary Examiner*—Mark F Huff
*Assistant Examiner*—Rachel L Burney
(74) *Attorney, Agent, or Firm*—Nixon & Vanderhye P.C.

(57) ABSTRACT

A hydrazone compound capable of realizing an electrophotographic photoreceptor having good electric properties such as good sensitivity and light responsibility, good electric and mechanical durability and good environment stability, is provided. The hydrazone compound is represented by the following general formula (1). The compound is contained in the charge transporting layer of the electrophotographic photoreceptor.

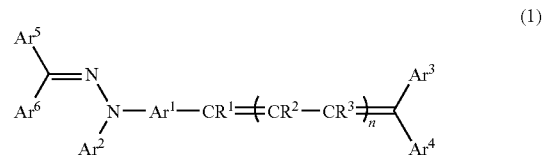

(1)

27 Claims, 3 Drawing Sheets

FOREIGN PATENT DOCUMENTS

| | | |
|---|---|---|
| JP | 58-198043 | 11/1983 |
| JP | 2-190862 | 7/1990 |
| JP | 5-66587 | 3/1993 |
| JP | 09-297415 | 11/1997 |
| JP | 10-161328 | 6/1998 |
| JP | 10161328 A * | 6/1998 |
| JP | 11-035540 | 2/1999 |
| JP | 11035540 A * | 2/1999 |
| JP | 2000-242007 | 9/2000 |
| JP | 2001305754 A * | 2/2001 |
| JP | 2002-055469 | 2/2002 |
| WO | WO 2004087641 * | 10/2004 |

* cited by examiner

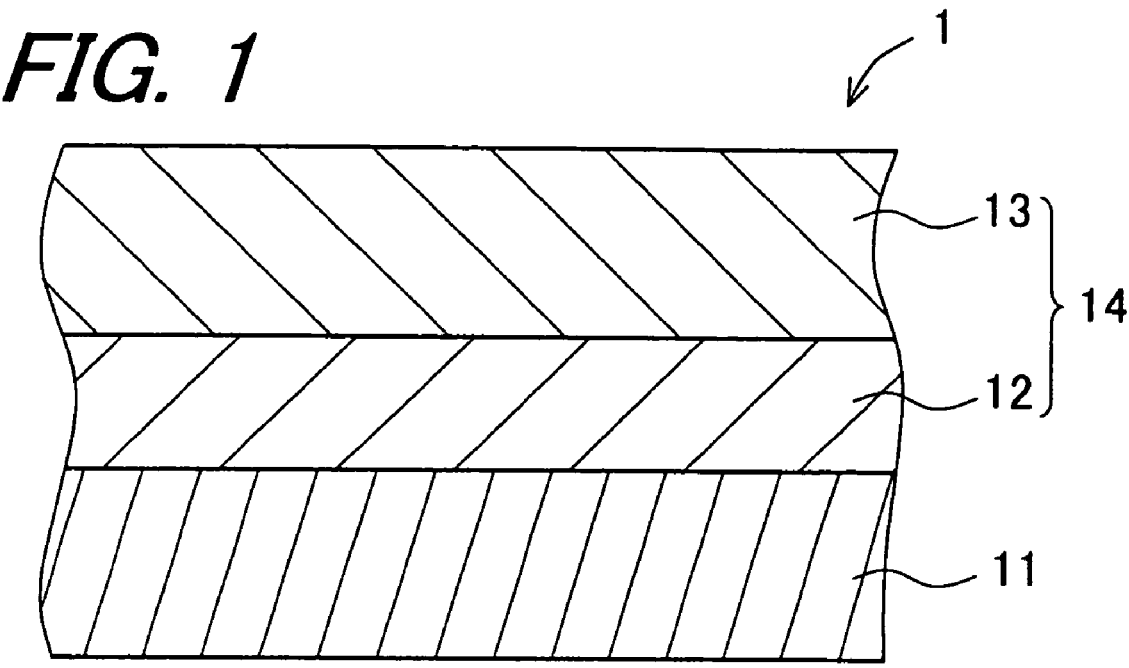
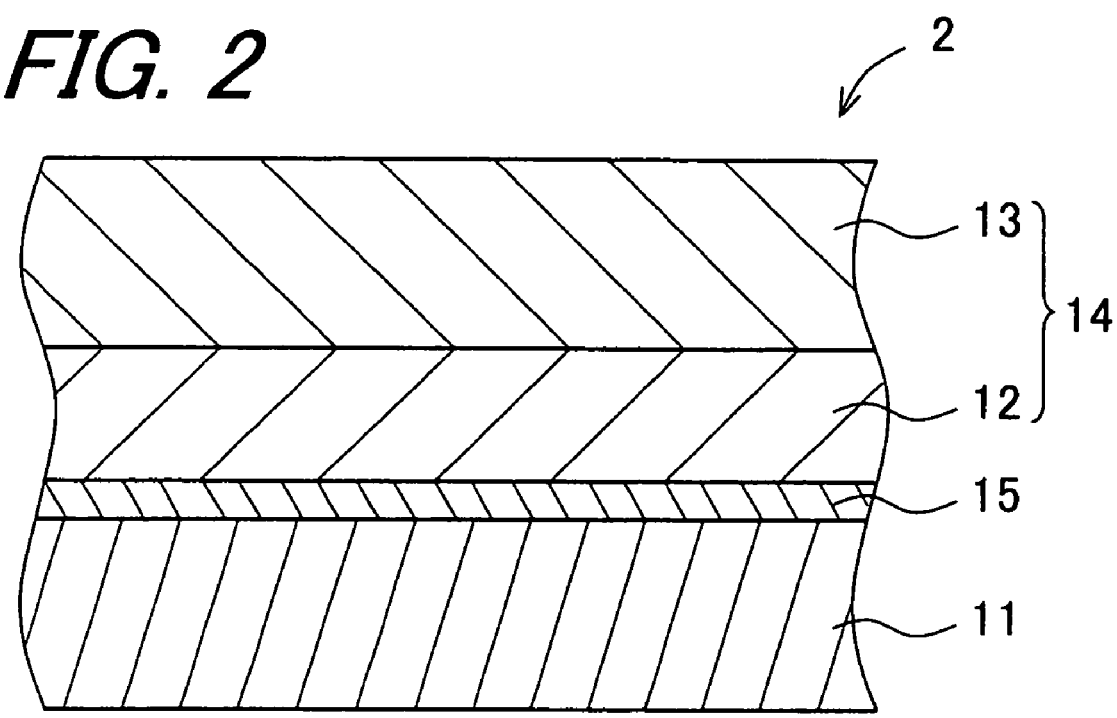

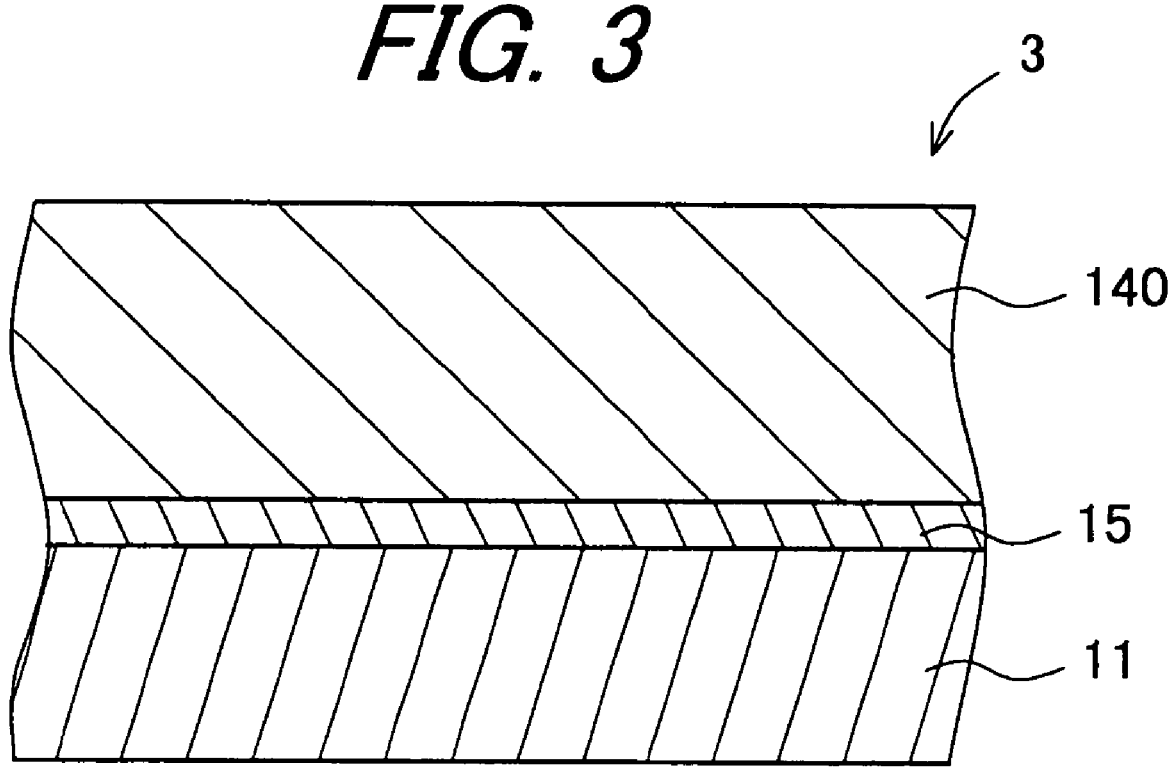

HYDRAZONE COMPOUND, ELECTROPHOTOGRAPHIC PHOTORECEPTOR COMPRISING THE HYDRAZONE COMPOUND, AND IMAGE FORMING APPARATUS EQUIPPED WITH THE ELECTROPHOTOGRAPHIC PHOTORECEPTOR

BACKGROUND OF THE INVENTION

1. Field of the Invention

The present invention relates to a hydrazone compound, an electrophotographic photoreceptor comprising the hydrazone compound, and an image forming apparatus equipped with the electrophotographic photoreceptor.

2. Description of the Related Art

An electrophotographic image forming apparatus for forming an image through electrophotography (hereinafter referred to as "electrophotographic apparatus") is much used as duplicators, printers, facsimiles, etc. In the electrophotographic apparatus, an image is formed according to an electrophotographic process as follows:

First, the photosensitive layer of an electrophotographic photoreceptor (this may be hereinafter simply referred to as "photoreceptor") is uniformly charged to a predetermined potential by charging means such as a charging roller and then exposed to light corresponding to the image information applied thereto by exposure means to thereby form an electrostatic latent image. A developer is applied to the thus-formed electrostatic latent image whereby the toner, a component of the developer is adhered to the surface of the photoreceptor to thereby develop the electrostatic latent image and visualize it as a toner image. Thus formed, the toner image is transferred onto a transfer material such recording paper from the surface of the photoreceptor by transfer means, and then fixed by fixing means. According to the process, an image is formed on a transfer material. On the other hand, the photoreceptor from which the toner image has been transferred is cleaned with cleaning means equipped with a cleaning blade or the like, whereby the toner still remaining on the surface of the photoreceptor not transferred to the transfer material during the transfer operation is removed. Next, the surface of the photosensitive layer is discharged by a discharger, and the electrostatic latent image thereon disappears.

The basic characteristics necessary for the photoreceptor for use in the electrophotographic process are that it has good electric properties, for example, it has good charge-retentive capability and hardly discharges in the dark while it has good photosensitivity and readily discharges through exposure to light. The others also necessary for the photoreceptor are that its electric properties as above are stable even in repeated service so that it can form homogeneous images for a long period of time, and it has good electric characteristic stability (this may be hereinafter simply referred to as "characteristic stability").

Recently, electrophotography is utilized not only in the field of duplicators but also in other fields of printing plate materials, slide films, microfilms and others for which silver salt photography has heretofore been used, and in addition, it is further applied to high-speed printers using a light source of laser, light-emitting diode (LED), cathode ray tube (CRT) or the like. With the expansion of the application field of electrophotography, requirements for electrophotographic photoreceptors are being high-leveled and broadened.

An electrophotographic photoreceptor is so designed that a photoconductive material-containing photosensitive layer is laminated on a photoconductive substrate. As the electrophotographic photoreceptor, conventionally broadly used is an inorganic photoreceptor equipped with a photosensitive layer comprising, as the main ingredient thereof, an inorganic photoconductive material such as selenium, zinc oxide or cadmium sulfide. The inorganic photoreceptor has basic properties as a photoreceptor in some degree, but has some drawbacks in that the film formation for the photosensitive layer is difficult, the plasticity is not good and the production costs are high. In addition, in general, inorganic photoconductive materials are highly toxic, and are therefore greatly limited in point of their production and use.

As described above, since the inorganic photoconductive material and the inorganic photoreceptor using the same involve many drawbacks, research and development have been progressed for organic photoconductive materials. Further, the organic photoconductive material has been studied and developed generally in recent years and it has been utilized not only for electrostatic recording devices such as the electrophotographic photoreceptor but also has been applied, for example, to sensor devices or organic Electro Luminescent (abbreviated as EL) devices.

The organic using the organic photoconductive material has advantages such that the film formation property for the photosensitive layer is favorable and the flexibility is excellent, as well as it is light in the weight, excellent in the transparency, and a photoreceptor showing good sensitivity to a wavelength region over a wide range can be designed easily by an appropriate sensitizing method. Thus, the organic photoreceptor has been under development as a predominant candidate for the electrophotographic photoreceptor.

In the early days, organic photoreceptors had some drawbacks in point of the sensitivity and the durability thereof, but these drawbacks have been significantly improved by development of a function-separated electrophotographic photoreceptor of which the charge generating function and the charge transporting function are separately attained by different substances. The function-separated photoreceptor of the type has, in addition to the above-mentioned advantages of organic photoreceptors, other advantages in that it has broad latitude in selecting the materials for the photosensitive layer and those having any desired characteristics are relatively readily produced.

The function-separated photoreceptor is grouped into a laminate-structured photoreceptor and a single-layered photoreceptor. In the function-separated photoreceptor of the single-layered function-separated photoreceptor, provided is a single-layered photosensitive layer where a charge generating substance having a charge generating function and a charge transporting substance having a charge transporting function are co-dispersed in a resin called binder resin having a binding function. In the laminate-structured function-separated photoreceptor, provided is a laminate-structured photosensitive layer that comprises a laminate structure of a charge generating layer with a charge generating substance dispersed in a binder resin and a charge transporting layer with a charge transporting substance dispersed in a binder resin.

Various substances have been investigated for the charge generating substance for use in the function-separated photoreceptor, and as those having good light resistance and good charge generating capability, proposed are various materials such as phthalocyanine pigments, squarylium dyes, azo pigments, perylene pigments, polycyclic quinone pigments, cyanine dyes, squaric acid dyes, pyrylium salt dyes.

Further, various compounds have been proposed as the charge transporting material, for example, pyrazoline compounds (for example, refer to Japanese Examined Patent publication JP-B2 52-4188 (1977)), hydrazone compounds (for example, refer to Japanese Unexamined Patent Publication JP-A 54-150128 (1979), Japanese Examined Patent Publication JP-B2 55-42380 (1980), Japanese Unexamined Patent Publication JP-A 55-52063 (1980)), triphenylamine compounds (for example, refer to Japanese Examined Patent Publication JP-B2 58-32372 (1983), and Japanese Unexamined Patent Publications JP-A 2-190862 (1990) and stilbene compounds (for example, Japanese Unexamined Patent Publications JP-A 54-151955 (1979) and JP-A 58-198043 (1983)).

The charge transporting substances must satisfy the following requirements:
(1) they are stable to light and heat,
(2) they are stable to active substances such as ozone, nitrogen oxide (chemical formula: $NO_x$) and nitric acid generated by corona discharging in charging the photoreceptor,
(3) they have high charge transporting ability,
(4) they have high compatibility with an organic solvent and a binder resin, and
(5) they can be manufactured easily and inexpensively.

However, while the charge transporting substances disclosed in, for example, the above-stated JP-B252-4188, JP-A54-150128, JP-B2 55-42380, JP-A 55-52063, JP-B2 58-32372, JP-A 2-190862, and JP-A 54-151955, JP-A 58-198043, can satisfy a portion of the demands but have not yet satisfy all of the demands at high level.

Further, in recent years, of the above-stated demands, particularly high charge transporting ability has been demanded for the charge transporting substance. For example, higher sensitivity has been demanded as the photoreceptor characteristics corresponding to the requirement of reduction in the size and high speed operation to electrophotographic apparatuses such as copying machines and printers, and the charge transporting ability of the charge transporting substance has been demanded to improve as means for attaining higher sensitivity of the photoreceptor.

Further, in the high speed electrophotographic process, since the time from exposure to the development is short, a photoreceptor of excellent light responsiveness has been required. In a case where the light responsiveness of the photoreceptor is poor, that is, the decaying speed of the surface potential of the photosensitive layer by exposure is slow, the residual potential rises and is used repetitively in a state where the surface potential is not decayed sufficiently. Therefore, the surface charges at a potion to be erased are not sufficiently erased by exposure to cause deterioration of the picture quality such as lowering of the image density in an early stage. In the function separated type photoreceptor, the charges generated from the charge generating substance upon light absorption are transported by the charge transporting substance to the surface of the photosensitive layer so that the surface charges of the photosensitive layer at a portion irradiated with a light are eliminated. Therefore, the light responsiveness depends on the charge transporting ability of the charge transporting substance. Accordingly, high charge transporting ability is required for the charge transporting substance also with a view point of attaining a photoreceptor having high light responsiveness and capable of forming high quality images also in a high speed electrophotographic process.

Further, high durability of the electrophotographic apparatus is also required. In order to attain the high durability, it is necessary that the electrophotographic photoreceptor has excellent durability to electric and mechanical external force and can operate stably for a long period of time. For example, as to the mechanical durability, durability of the surface layer of the photoreceptor is important. In a case where a photoreceptor is used being mounted on an electrophotographic apparatus, the surface layer of the photoreceptor is inevitably scraped at a portion thereof by a contact member such as a cleaning blade or a charge roller. In a case where the amount of film reduction on the surface layer of the photoreceptor is large, since the charge retainability of the photoreceptor is lowered failing to provide high quality images. Accordingly, in order to attain higher durability of the electrophotographic apparatus, it is demanded for a photoreceptor having a surface layer of high mechanical durability resistant to the contact member, that is, having a surface layer of high printing resistance with less amount of film reduction.

As the charge transporting substances satisfying such requirements, proposed are compounds having both a hydrazone structure and a styryl structure (see Japanese Unexamined Patent Publication JP-A 5-66587 (1993)). However, with the recent increase in the requirements for small-sized, high-speed and durable electrophotographic apparatus, desired is development of charge transporting substances having further better charge transporting capability, and there is room for improvement in the charge transporting substances disclosed in JP-A 5-66587.

Electrophotographic apparatus are desired to be able to provide homogeneous images irrespective of the service environment. Accordingly, photoreceptors are required to have good environment stability in that their properties change a little depending on the fluctuation of the ambient environment such as temperature and humidity. For example, photoreceptors are desired not to cause sensitivity reduction even when used in low-temperature environments. To realize such photoreceptors, charge transporting substances are required to have good charge transporting capability.

SUMMARY OF THE INVENTION

An object of the invention is to provide an organic photoconductive material having good charge transporting capability and capable of realizing electrophotographic photoreceptors of high reliability, having good electric properties such as sensitivity and light responsibility and having good electric and mechanical durability and good environment stability, and also to provide an electrophotographic photoreceptor comprising the organic photoconductive material and an image forming apparatus equipped with the photoreceptor.

The present inventors have assiduously studied for the purpose of solving the above problems and, as a result, have found out a novel hydrazone compound having both a hydrazone structure and a diene structure or a triene structure as an effective organic photoconductive material, and have completed the invention.

Specifically, the invention provides a hydrazone compound of a general formula (1):

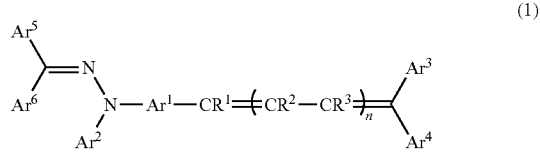

wherein $Ar^1$ represents an arylene group optionally having a substituent; $Ar^2$ represents an aryl, heterocyclic, aralkyl or alkyl group optionally having a substituent; $Ar^3$ represents an aryl, heterocyclic, aralkyl or thienylalkyl group optionally having a substituent; $Ar^4$ represents a hydrogen atom, or an aryl, heterocyclic, aralkyl or alkyl group optionally having a substituent; $Ar^5$ represents an aryl or heterocyclic group optionally having a substituent; $Ar^6$ represents a hydrogen atom, or an aryl, heterocyclic, aralkyl or alkyl group optionally having a substituent; with the proviso that, to the carbon atom to which the group $=CAr^3Ar^4$ bonds, a divalent aromatic or heterocyclic group may bond in place of the group $=CAr^3Ar^4$ bonds; to the nitrogen atom to which $=CAr^5Ar^6$ bonds, a divalent aromatic or heterocyclic group may bond in place of the group $=CAr^5Ar^6$ bonds; $R^1$, $R^2$ and $R^3$ may be the same or different, each representing a hydrogen atom, or an alkyl, aryl, heterocyclic or aralkyl group optionally having a substituent; n indicates 1 or 2; when n is 2, then two $R^2$s and two $R^3$s each may be the same or different.

In the invention, it is preferable that the hydrazone compound is one represented by the following general formula (2):

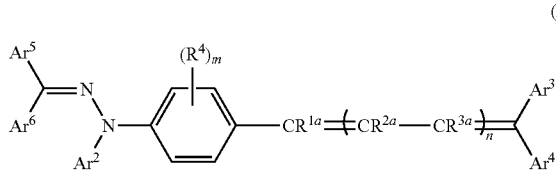

(2)

wherein $Ar^2$, $Ar^3$, $Ar^4$, $Ar^5$, $Ar^6$ and n have the same meanings as in formula (1); $R^{1a}$ represents a hydrogen atom, or a C1-3 alkyl or aryl group optionally having a substituent; one of $R^{2a}$ and $R^{3a}$ is a hydrogen atom, and the other is a C1-3 alkyl, heterocyclic or aralkyl group optionally having a substituent, provided that, when n is 2, then two $R^{2a}$s and two $R^{3a}$s each may be the same or different; $R^4$ represents a hydrogen atom, a halogen atom, a C1-5 perfluoroalkyl group, or a C1-3 alkyl, C1-3 alkoxy, C1-5 fluoroalkyl or C2-8 dialkylamino group optionally having a substituent; m indicates an integer of from 1 to 4, provided that when m is 2 or more, then plural $R^4$s may be the same or different.

Also in the invention, it is preferable that in formula (2), $Ar^5$ is an aryl group optionally having one or more substituents selected from a halogen atom, an alkyl group, an alkoxy group, a perhalogenoalkyl group, a halogenoalkyl group, a dialkylamino group, a styryl group and a phenylthio group, or a monocyclic or condensed-cyclic heterocyclic group optionally having an alkyl group as the substituent thereof and containing one or more hetero atoms selected from oxygen, nitrogen and sulfur atoms.

Also in the invention, it is preferable that the hydrazone compound of the invention is one represented by the following general formula (3):

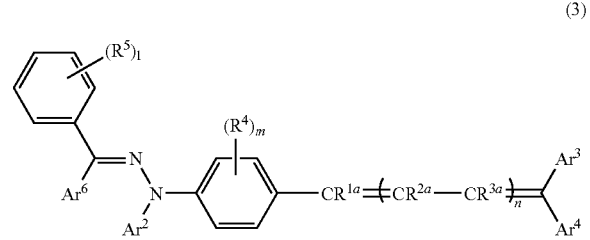

(3)

wherein $Ar^2$, $Ar^3$, $Ar^4$, $Ar^6$ and n have the same meanings as in formula (1); $R^{1a}$, $R^{2a}$, $R^{3a}$, $R^4$ and m have the same meanings as in formula (2); $R^5$ represents a hydrogen atom, a halogen atom, a C1-3 alkyl group, a C1-3 alkoxy group, a C1-5 perfluoroalkyl group, a C1-5 fluoroalkyl group, or a C2-8 dialkylamino group; 1 indicates an integer of from 1 to 5, provided that when 1 is 2 or more, then plural $R^5$s may be the same or different; and the phenyl group to which $R^5$ bonds, and $Ar^6$ may form a condensed ring along with the carbon atoms to which they bond.

Also in the invention, it is preferable that in formula (3), $R^5$ is a hydrogen atom, a C1-3 alkyl group, or a C1-3 alkoxy group.

Also in the invention, it is preferable that in formula (3), $Ar^2$ is a C1-3 alkyl group, a phenyl group optionally having a halogen atom, a C-13 alkyl group or a phenylthio group as the substituent thereof, a benzyl group optionally having a C1-3 alkoxy group as the substituent thereof, or a monocyclic or condensed-cyclic heterocyclic group optionally having a C1-3 alkyl group as the substituent thereof and having one or two hetero atoms selected from sulfur and nitrogen atoms;

$Ar^3$ is a phenyl group optionally having a C1-3 alkyl group, a C1-3 alkoxy group or a C1-3 halogenoalkyl group as the substituent thereof, an aralkyl group where the alkyl moiety has from 1 to 2 carbon atoms, a thienylalkyl group where the alkyl moiety has from 1 to 3 carbon atoms, or a monocyclic or condensed-cyclic heterocyclic group optionally having a C1-3 alkyl group as the substituent thereof and having one or more hetero atoms selected from oxygen, sulfur and nitrogen atoms;

$Ar^4$ is a hydrogen atom, a C1-3 alkyl group, or a phenyl group optionally having a C1-3 alkyl group, a C1-3 alkoxy group or a dialkylamino group where the alkyl moiety has from 1 to 3 carbon atoms, as the substituent thereof;

$Ar^6$ is a hydrogen atom, a C1-3 alkyl group, or a monocyclic heterocyclic group containing an oxygen atom as the hetero atom therein;

$R^{1a}$ is a hydrogen atom, a C1-3 alkyl group, or a phenyl group;

one of $R^{2a}$ and $R^{3a}$ is a hydrogen atom, and the other is a hydrogen atom, a C1-3 alkyl group, a benzyl group, or a monocyclic heterocyclic group containing a sulfur atom as the hetero atom therein; and $R^4$ is a hydrogen atom, or a C1-3 alkyl group.

Also in the invention, it is preferable that in formula (3), $R^{1a}$, $R^{2a}$ and $R^{3a}$ are all hydrogen atoms.

In addition, the invention provides an electrophotographic photoreceptor comprising:

a conductive substrate; and a photosensitive layer provided on the conductive substrate, wherein the photosensitive layer contains the hydrazone compound of the invention.

In the invention it is preferable that the photosensitive layer further contains an oxotitanium phthalocyanine compound.

Also in the invention, it is preferable that the oxotitanium phthalocyanine compound has a crystal structure that shows a diffraction peak at least at a Bragg angle 2θ (error: 2θ±0.2°) of 27.2° in the X-ray diffraction spectrum thereof to a Cu—Kα characteristic X ray (wavelength: 1.54 angstroms)

Also in the invention, it is preferable that the photosensitive layer comprises a charge generating layer containing a charge generating substance and a charge transporting layer containing a charge transporting substance, and the charge transporting substance contains the hydrazone compound of the invention.

Also in the invention it is preferable that the charge transporting layer further contains a binder resin, and the ratio of the weight (B) of the binder resin to the weight (A) of the hydrazone compound of the invention in the charge transporting layer, (B/A) is from 1.2 to 3.0.

Also in the invention it is preferable that the electrophotographic photoreceptor further comprises an intermediate layer provided between the conductive substrate and the photosensitive layer.

In addition, the invention provides an image forming apparatus, comprising:

the electrophotographic photoreceptor mentioned above;

charging means for charging the electrophotographic photoreceptor;

exposing means for exposing the charged electrophotographic photoreceptor to light; and developing means for developing the electrostatic latent image formed through exposure.

According to the invention, there is provided a hydrazone compound having a specific structure represented by the general formula (1). The hydrazone compound of formula (1) of the invention has excellent charge transporting capability, especially excellent hole-transporting capability, and is therefore favorable as a charge transporting substance for electrostatic recording devices for electrophotographic photoreceptors and for other devices such as sensor devices, EL devices. Using the hydrazone compound of the invention in these devices allow to make the devices have excellent responsibility. For example, when the hydrazone compound of the invention is used in the photosensitive layer of an electrophotographic photoreceptor, then it is possible to realize an electrophotographic photoreceptor having good electric properties such as good chargeability, sensitivity and light responsibility, having good electric and mechanical durability and having good environment stability.

Of the hydrazone compounds of formula (1) of the invention, specific ones mentioned above are preferred. Since these hydrazone compounds have especially excellent charge transporting capability and are therefore especially effective as a charge transporting substance in devices such as electrophotographic photoreceptors.

The photosensitive layer of the electrophotographic photoreceptor of the invention contains the hydrazone compound of formula (1) of the invention and it functions as a charge transporting substance. Accordingly, the electrophotographic photoreceptor of the invention has good electric properties such as good chargeability, sensitivity and light responsibility and has good electric durability and environment stability, and therefore has high reliability. Even when used in a high-speed electrophotographic process, the electrophotographic photoreceptor realizes the advantage of not causing image quality deterioration. Accordingly, using the electrophotographic photoreceptor of the invention makes it possible to stably provide high-quality images for a long period of time in various environments. In addition, using the electrophotographic photoreceptor of the invention also makes it possible to further increase the image-forming speed without worsening the quality of the images formed.

The photosensitive layer of the electrophotographic photoreceptor of the invention may contain an oxotitanium phthalocyanine compound. Containing the compound, the sensitivity and the resolution of the electrophotographic photoreceptor may be further increased.

Preferably for use in the invention, the oxotitanium phthalocyanine compound has a crystal structure that shows a diffraction peak at least at a Bragg angle $2\theta$ (error: $2\theta \pm 0.2°$) of $27.2°$ in the X-ray diffraction spectrum thereof to a Cu—K$\alpha$ characteristic X ray (wavelength: 1.54 angstroms). The oxotitanium phthalocyanine compound of the type has especially excellent charge generating capability and charge-injecting capability. Accordingly, using the oxotitanium phthalocyanine compound of the type allows to further increase the sensitivity and the resolution of the electrophotographic photoreceptor containing it.

Preferably, the photosensitive layer of the electrophotographic photoreceptor of the invention comprises a charge generating layer containing a charge generating substance and a charge transporting layer containing a charge transporting substance containing the hydrazone compound of the invention. The constitution that comprises such different layers individually participating in the charge generating function and the charge transporting function allows to independently select the materials for the respective layers and therefore the materials most favorable to the charge generating function and to the charge transporting function can be selected. Accordingly, the electric properties such as the chargeability, the sensitivity and the light responsibility, as well as the electric and mechanical durability of the electrophotographic photoreceptor may be further improved.

Preferably in the invention, the ratio of the weight (B) of the binder resin to the weight (A) of the hydrazone compound of the invention in the charge transporting layer, (B/A) is from 1.2 to 3.0. This embodiment further improves the printing durability of the charge transporting layer. In addition, since the hydrazone compound of the invention in the charge transporting layer has excellent charge transporting capability, the responsibility of the electrophotographic photoreceptor does not lower even through the binder resin is in the charge transporting layer in the ratio as above. Accordingly, the electrophotographic photoreceptor of the invention has the advantage in that the printing durability of the charge transporting layer thereof may be improved and the mechanical durability may also be improved without lowering the light responsibility of the photoreceptor.

Also preferably in the invention, an intermediate layer is provided between the conductive substrate and the photosensitive layer. This constitution allows to prevent charge injection from the conductive substrate to the photosensitive layer, preventing the formation of image defects. The embodiment of providing an intermediate layer between the conductive substrate and the photosensitive layer may lower the sensitivity of the photoreceptor. However, since the electrophotographic photoreceptor of the invention contains the hydrazone compound of the invention as the charge transporting substance in the photosensitive layer, it may still have good sensitivity even though the intermediate layer is provided therein. Accordingly, the electrophotographic photoreceptor of the invention may have an intermediate layer without lowering the sensitivity thereof, and may prevent the formation of image defects.

The image forming apparatus of the invention comprises the electrophotographic photoreceptor of the invention. Since the electrophotographic photoreceptor of the invention contains the hydrazone compound of formula (1) of the invention in the photosensitive layer, it has good electric properties such as good chargeability, sensitivity and light responsibility, good electric and mechanical durability and good environment stability. Accordingly, the invention realizes an image forming apparatus of high reliability capable of stably forming high-quality images for a long period of time in various environments. In addition, since the electrophotographic photoreceptor of the invention does not cause image quality deterioration even though used in a high-speed electrophotographic process, the image forming apparatus of the invention is applicable to high-speed image formation.

BRIEF DESCRIPTION OF THE DRAWINGS

Other and further objects, features, and advantages of the invention will be more explicit from the following detailed description taken with reference to the drawings wherein:

FIG. 1 is a fragmentary cross sectional view schematically showing the constitution of an electrophotographic photoreceptor as a first embodiment of electrophotographic photoreceptor according to the invention;

FIG. 2 is a fragmentary cross sectional view schematically showing the constitution of an electrophotographic photoreceptor as a second embodiment of electrophotographic photoreceptor according to the invention;

FIG. 3 is a fragmentary cross sectional view schematically showing the constitution of an electrophotographic photoreceptor as a third embodiment of electrophotographic photoreceptor according to the invention.

DETAILED DESCRIPTION

Figure 4:
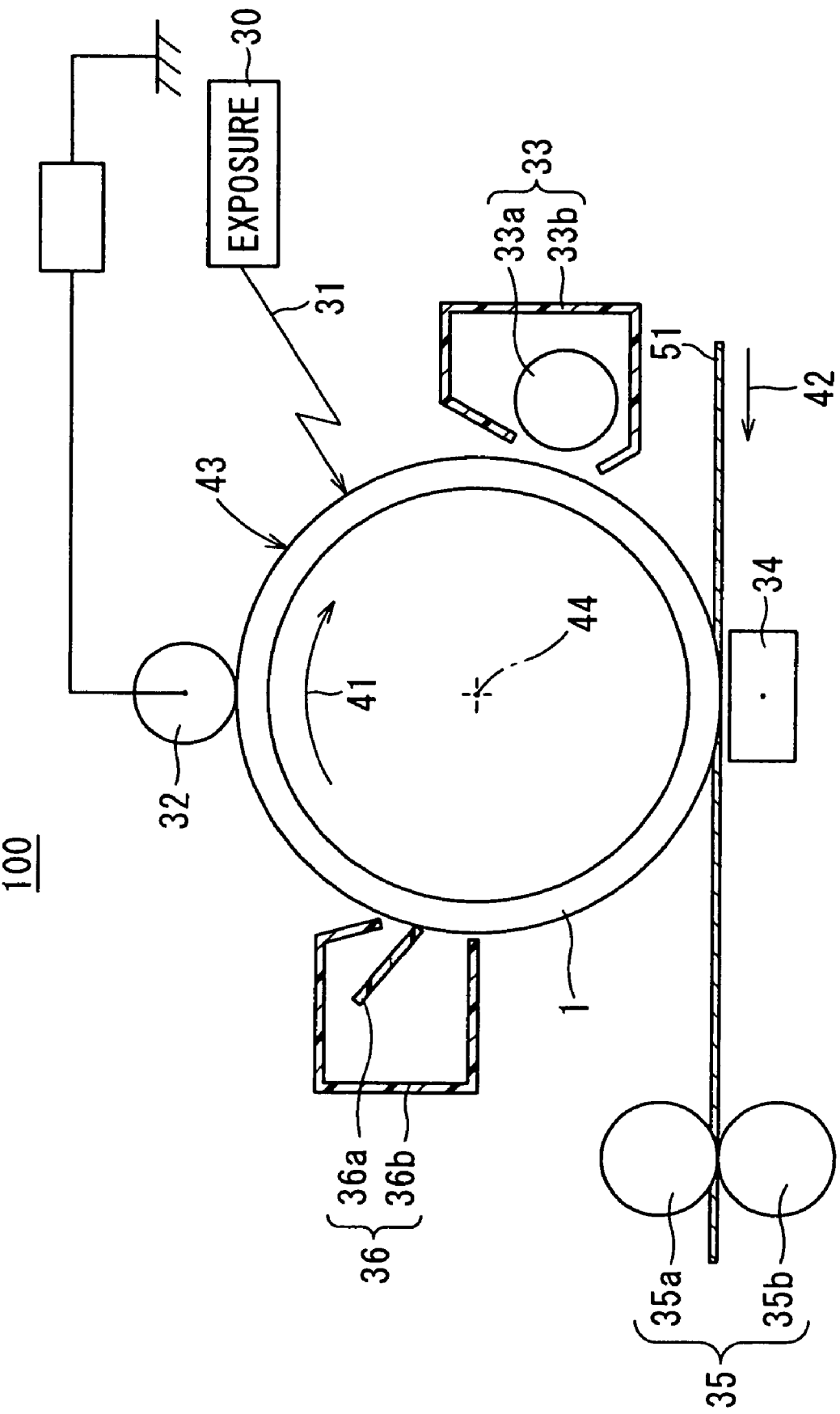
FIG. 4 is a side elevational view for the arrangement schematically showing the constitution of an image forming apparatus as an embodiment of image forming apparatus according to the invention.

Now referring to the drawings, preferred embodiments of the invention are described below.

The hydrazone compound of the invention is represented by the following general formula (1):

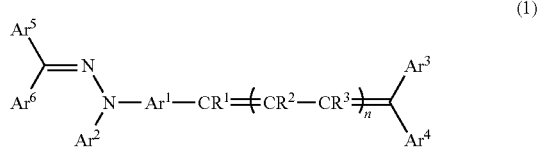

In formula (1), $Ar^1$ represents an arylene group optionally having a substituent. The arylene group includes a phenylene group such as p-phenylene group, and m-phenylene group; a naphthylene group such as 1,4-naphthylene group; and a biphenylene group such as 4,4'-biphenylene group.

The substituent which the arylene group may have includes a halogen atom such as fluorine atom, chlorine atom, and bromine atom; a perfluoroalkyl group (preferably a C1-5 perfluoroalkyl group) such as perfluoromethyl group; an alkyl group (preferably a C1-3 alkyl group) such as methyl group, and ethyl group; an alkoxy group (preferably a C1-3 alkoxy group) such as methoxy group, and ethoxy group; a fluoroalkyl group (preferably a C1-5 fluoroalkyl group) such as monofluoromethyl group, and 1,1-difluoroethyl group; a dialkylamino group (preferably a C2-8 dialkylamino group) such as dimethylamino group, and diethylamino group. These substituents may further have a substituent.

In formula (1), $Ar^2$ represents an aryl group optionally having a substituent, a heterocyclic group optionally having a substituent, an aralkyl group optionally having a substituent, or an alkyl group optionally having a substituent.

Specific examples of the groups for $Ar^2$ are mentioned below. The aryl group includes a monocyclic or polycyclic aryl group having from 1 to 6 rings (preferably from 1 to 4 rings), such s phenyl group, naphthyl group, biphenylyl group. The heterocyclic group includes a monocyclic or condensed-cyclic heterocyclic group containing, as the hetero atom thereof, an oxygen, nitrogen, sulfur, selenium or tellurium atom, such as furyl group, thienyl group, thiazolyl group, benzofuryl group, and benzothiophenyl group. The condensed-cyclic heterocyclic group as referred to herein is meant to indicate a condensation of monocyclic hetero rings, or a condensation of an aromatic ring and a heterocyclic ring. The aralkyl group may be one where the alkyl moiety has 1 or 2 carbon atoms, such as benzyl group, phenethyl group, and 1-naphthylmethyl group. The alkyl group includes a straight chain alkyl group having from 1 to 3 carbon atoms such as methyl group, ethyl group, and propyl group; a branched chain alkyl group having from 1 to 3 carbon atoms such as isopropyl group; and a cycloalkyl group having from 5 to 8 carbon atoms such as cyclohexyl group, and cyclopentyl group. For the substituent which these groups may have, referred to are the substituents mentioned above for the arylene group for $Ar^1$.

In formula (1), $Ar^3$ represents an aryl group optionally having a substituent, a heterocyclic group optionally having a substituent, an aralkyl group optionally having a substituent, or a thienylalkyl group optionally having a substituent.

Specific examples of the aryl group, the heterocyclic group and the aralkyl group for $Ar^3$ may be the same as those mentioned above for the aryl group, the heterocyclic group and the aralkyl group for $Ar^2$. Specific examples of the thienylalkyl group are those where the alkyl moiety has from 1 to 3 carbon atoms, such as thienylmethyl group, and thienylethyl group. For the substituent which these groups may have, referred to are the substituents mentioned above for the arylene group for $Ar^1$.

In formula (1), $Ar^4$ represents a hydrogen atom, an aryl group optionally having a substituent, a heterocyclic group optionally having a substituent, an aralkyl group optionally having a substituent, or an alkyl group optionally having a substituent. Specific examples of the groups for $Ar^4$ may be the same as those mentioned above for $Ar^2$. For the substituent which these groups may have, referred to are the substituents mentioned above for the arylene group for $Ar^1$.

In formula (1), $Ar^5$ represents an aryl group optionally having a substituent, or a heterocyclic group optionally having a substituent. Specific examples of the aryl group and the heterocyclic group for $Ar^5$ may be the same as those mentioned above for the aryl group and the heterocyclic group for Ar For the substituent which these groups may have, referred to are the substituents mentioned above for the arylene group for $Ar^1$.

In formula (1), $Ar^6$ represents a hydrogen atom, an aryl group optionally having a substituent, a heterocyclic group optionally having a substituent, an aralkyl group optionally having a substituent, or an alkyl group optionally having a substituent. Specific examples of these groups for $Ar^6$ may be the same as those mentioned above for $Ar^2$. For the substituent which these groups may have, referred to are the substituents mentioned above for the arylene group for $Ar^1$.

In formula (1), to the carbon atom to which the group $=CAr^3Ar^4$ bonds, a divalent aromatic or heterocyclic group may bond in place of the group $=CAr^3Ar^4$ bonds. The divalent aromatic group includes a 1-indanylidene group, and a 1,2,3,4-tetrahydro-1-naphthyridine group. The divalent heterocyclic group includes a benzosuberonylidene group, and a 9-xanthenylidene group.

In formula (1), to the nitrogen atom to which the group $=CAr^5Ar^6$ bonds, a divalent aromatic or heterocyclic group may bond in place of the group $=CAr^5Ar^6$ bonds. For the divalent aromatic or heterocyclic group that may bond to the nitrogen atom to which the group $=CAr^5Ar^6$ bonds, referred to are those mentioned herein above for the divalent aromatic or heterocyclic group that may bond to the nitrogen atom to which the group =CAr3Ar⁴ bonds.

In formula (1), $R^1$, $R^2$ and $R^3$ may be the same or different, each representing a hydrogen atom, an alkyl group optionally having a substituent, an aryl group optionally having a substituent, a heterocyclic group optionally having a substituent, or an aralkyl group optionally having a substituent. Specific examples of the groups for $R^1$, $R^2$ and $R^3$ may be the same as those mentioned above for $Ar^2$. For the substituent which these groups may have, referred to are the substituents mentioned above for the arylene group for $Ar^1$.

In formula (1), n indicates 1 or 2; when n is 2, then two $R^2$'s and two $R^3$'s each may be the same or different.

The hydrazone compound of formula (1) of the invention has excellent charge transporting capability, especially excellent hole-transporting capability. The reason why the hydrazone compound of the invention could have such excellent charge transporting capability would be because a conjugated system is formed in a broad range inside the molecule. To that effect, since the hydrazone compound of the invention has excellent charge transporting capability, it is suitable to use as a charge transporting substance. For example, using the hydrazone compound of the invention as the charge transporting substance in devices such as electrostatic recording devices for electrophotographic photoreceptors, as well as sensor devices or EL devices allows to realize devices of good responsibility.

Of the hydrazone compounds of formula (1), preferred are those of the following general formula (2):

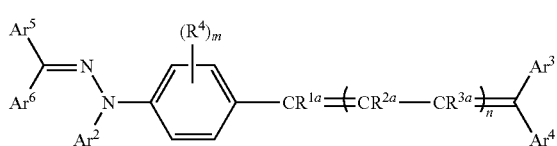

(2)

In formula (2), $Ar^2$, $Ar^3$, $Ar^4$, $Ar^5$, $Ar^6$ and n have the same meanings as in formula (1).

In formula (2), $R^{1a}$ represents a hydrogen atom, a C1-3 alkyl group optionally having a substituent, or an aryl group optionally having a substituent. The C1-3 alkyl group includes a straight chain alkyl group having from 1 to 3 carbon atoms such as methyl group, ethyl group, and n-propyl group; and a branched chain alkyl group having from 1 to 3 carbon atoms such as isopropyl group. The aryl group may be a monocyclic or polycyclic aryl group having from 1 to 6 rings (preferably from 1 to 4 rings), such as phenyl group, naphthyl group, and biphenyl group. For the substituent which these groups may have, referred to are the substituents mentioned above for the arylene group for $Ar^1$.

In formula (2), one of $R^{2a}$ and $R^{3a}$ is a hydrogen atom, and the other is a C1-3 alkyl group optionally having a substituent, a heterocyclic group optionally having a substituent or an aralkyl group optionally having a substituent, provided that, when n is 2, then two $R^{2a}$'s and two $R^{3a}$'s each may be the same or different.

For the C1-3 alkyl group for $R^{2a}$ and $R^{3a}$, referred to are those mentioned hereinabove for the C1-3 alkyl group for $R^{1a}$. The heterocyclic group may be a 5-membered or 6-membered, or condensed-cyclic heterocyclic group having, as the hetero atom thereof, an oxygen, nitrogen, sulfur, selenium or tellurium atom, such as furyl group, thienyl group, thiazolyl group, benzofuryl group, and benzothiophenyl group. The aralkyl group may be one in which the alkyl moiety has 1 or 2 carbon atoms, such as benzyl group, phenethyl group, and 1-naphthylmethyl group. For the substituent which these groups may have, referred to are the substituents mentioned above for the arylene group for $Ar^1$.

In formula (2), $R^4$ represents a hydrogen atom, a halogen atom, a C1-5 perfluoroalkyl group, a C1-3 alkyl group optionally having a substituent, a C1-3 alkoxy group optionally having a substituent, a C1-5 fluoroalkyl group optionally having a substituent or a C2-8 dialkylamino group optionally having a substituent; m indicates an integer of from 1 to 4, provided that when m is 2 or more, then plural $R^4$'s may be the same or different.

Specific examples of the groups for $R^4$ are mentioned below. The halogen atom includes a fluorine atom, a bromine atom, and a chlorine atom. The C1-5 perfluoroalkyl group includes a trifluoromethyl group, a pentafluoroethyl group, and a heptafluoropropyl group. The C1-3 alkyl group includes a straight chain alkyl group having from 1 to 3 carbon atoms such as methyl group, ethyl group, and n-propyl group; and a branched chain alkyl group having from 1 to 3 carbon atoms such as isopropyl group. The C1-3 alkoxy group includes a straight chain alkoxy group having from 1 to 3 carbon atoms such as methoxy group, ethoxy group, and n-propoxy group; and a branched chain alkoxy group having from 1 to 3 carbon atoms such as isopropoxy group. The C1-5 fluoroalkyl group includes a monofluoromethyl group, a 1,1-difluoroethyl group, and a 1,1,1-trifluorobutyl group. The C2-8 dialkylamino group includes a dimethylamino group, a diethylamino group, and a diisopropylamino group. For the substituent which these groups may have, referred to are the substituents mentioned above for the arylene group for $Ar^1$.

Of the hydrazone compounds of formula (1) of the invention, those of formula (2) have especially excellent charge transporting capability and are especially effective as a charge transporting substance.

Of the hydrazone compounds of formula (2), more preferred are those where $Ar^5$ is an aryl group optionally having one or more substituents selected from a halogen atom, an alkyl group, an alkoxy group, a perhalogenoalkyl group, a halogenoalkyl group, a dialkylamino group, a styryl group and a phenylthio group, or a monocyclic or condensed-cyclic heterocyclic group optionally having an alkyl group as the substituent thereof and containing one or more hetero atoms selected from oxygen, nitrogen and sulfur atoms.

Even more preferred are hydrazone compounds of the following general formula (3):

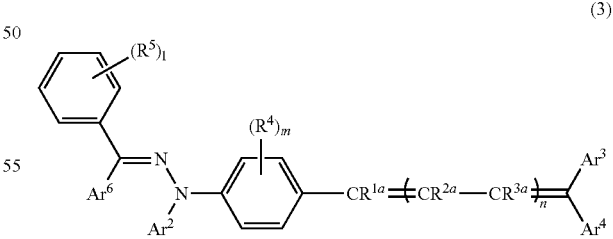

(3)

In formula (3), $Ar^2$, $Ar^3$, $Ar^4$, $Ar^6$ and n have the same meanings as in formula (1); $R^{1a}$, $R^{2a}$, $R^{3a}$, $R^4$ and m have the same meanings as in formula (2).

In formula (3), $R^5$ represents a hydrogen atom, a halogen atom, a C1-3 alkyl group, a C1-3 alkoxy group, a C1-5 perfluoroalkyl group, a C1-5 fluoroalkyl group, or a C2-8 dialkylamino group; l indicates an integer of from 1 to 5, provided that when l is 2 or more, then plural $R^5$'s may be the same or different. For the specific examples of the groups for $R^5$, referred to are those mentioned above for the groups for $R^4$ in formula (2).

In formula (3), the phenyl group to which $R^5$ bonds, and $Ar^6$ may form a condensed ring along with the carbon atoms to which they bond. The condensed ring includes indane and 1,2,3,4-tetrahydronaphthalene.

The hydrazone compounds of formula (3) may be produced inexpensively from easily-available benzoyl derivatives with various substituents introduced thereinto, as the hydrazone intermediates of a general formula (4) mentioned below. Accordingly, using the hydrazone compound of formula (3) allows to inexpensively provide devices such as electrophotographic photoreceptors of good responsibility.

Of the hydrazone compounds of formula (3), more preferred are those where $R^5$ is a hydrogen atom, a C1-3 alkyl group, or a C1-3 alkoxy group.

Of the hydrazone compounds of formula (3), even more preferred are those where Ar is a C1-3 alkyl group, a phenyl group optionally having a halogen atom, a C-13 alkyl group or a phenylthio group as the substituent thereof, a benzyl group optionally having a C1-3 alkoxy group as the substituent thereof, or a monocyclic or condensed-cyclic heterocyclic group optionally having a C1-3 alkyl group as the substituent thereof and having one or two hetero atoms selected from sulfur and nitrogen atoms; $Ar^3$ is a phenyl group optionally having a C1-3 alkyl group, a C1-3 alkoxy group or a C1-3 halogenoalkyl group as the substituent thereof, an aralkyl group where the alkyl moiety has 1 or 2 carbon atoms, a thienylalkyl group where the alkyl moiety has from 1 to 3 carbon atoms, or a monocyclic or condensed-cyclic heterocyclic group optionally having a C1-3 alkyl group as the substituent thereof and having one or more hetero atoms selected from oxygen, sulfur and nitrogen atoms; $Ar^4$ is a hydrogen atom, a C1-3 alkyl group, or a phenyl group optionally having a C1-3 alkyl group, a C1-3 alkoxy group or a dialkylamino group where the alkyl moiety has from 1 to 3 carbon atoms, as the substituent thereof; $Ar^6$ is a hydrogen atom, a C1-3 alkyl group, or a monocyclic heterocyclic group containing an oxygen atom as the hetero atom therein; $R^{1a}$ is a hydrogen atom, a C1-3 alkyl group, or a phenyl group; one of $R^{2a}$ and $R^{3a}$ is a hydrogen atom, and the other is a hydrogen atom, a C1-3 alkyl group, a benzyl group, or a monocyclic heterocyclic group containing a sulfur atom as the hetero atom therein; and $R^4$ is a hydrogen atom, or a C1-3 alkyl group.

Still more preferred are compounds of formula (3) where $R^{1a}$, $R^{2a}$ and $R^{3a}$ are all hydrogen atoms.

Specific examples of the hydrazone compounds of formula (1) of the invention are Compounds No. 1 to No. 60 shown in Table 1 to Table 4 below, to which, however, the hydrazone compounds of the invention should not be limited.

In Table 1 to Table 4, the compounds are expressed by the structural groups constituting them. For example, Compound No. 1 in Table 1 is a hydrazone compound having the following structural formula (1a):

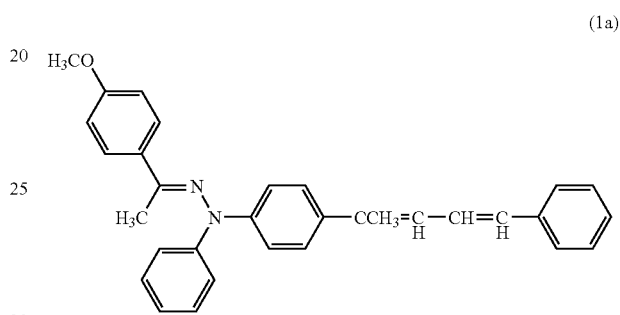

(1a)

In Table 1 to Table 4 that show compounds of formula (1) in which a divalent aromatic or heterocyclic group bonds to the carbon atom in place of the group $=CAr^3Ar^4$, the divalent group is given in the columns for $Ar^3$ and $Ar^4$. In these that show compounds of formula (1) in which a divalent aromatic or heterocyclic group bonds to the carbon atom in place of the group $=CAr^5Ar^6$, the divalent group is given in the columns for $Ar^5$ and $Ar^6$. In these that show compounds of formula (1) where n=2 and where two $R^2$'s are the same and two $R^3$'s are the same, then one $R^2$ and one $R^3$ are shown.

TABLE 1

| Compound No. | N—$Ar^1$— | $Ar^2$ | $R^1$ | n | $CR^2$—$CR^3$ | $Ar^3$ |
|---|---|---|---|---|---|---|
| 1 | N—⌬— | ⌬ | —$CH_3$ | 1 | CH—CH | ⌬ |
| 2 | N—⌬— | $H_3C$—⌬— | H | 1 | CH—CH | ⌬—$CH_3$ |
| 3 | N—⌬— | naphthyl | H | 1 | CH—CH | ⌬—$OCH_3$ |
| 4 | N—⌬— | $H_3CO$—⌬— | H | 1 | CH—CH | ⌬—$N(CH_3)_2$ |

TABLE 1-continued
| 5 | 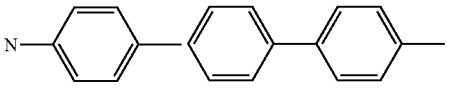 | 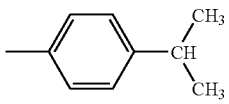 | H | 1 | CH—CH |  |
| 6 | 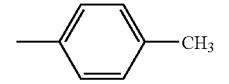 | —CH₃ | H | 1 | CH—CH |  |
| 7 | 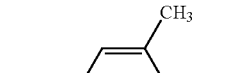 | —C₂H₅ | H | 1 | CH—CH |  |
| 8 | 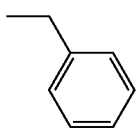 | 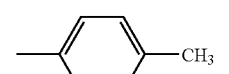 | H | 1 | CH—CH | 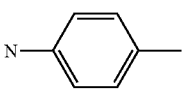 |
| 9 | 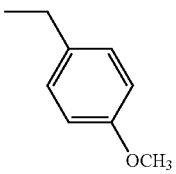 | 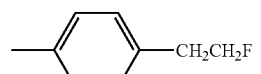 | H | 1 | CH—CH | 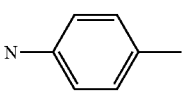 |
| 10 | 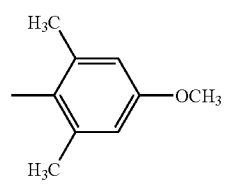 | —CH(CH₃)₂ | H | 1 | CH—CH | 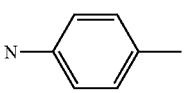 |
| 11 | 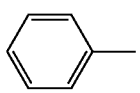 | 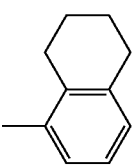 | H | 1 | CH—CH | 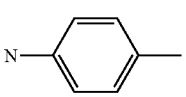 |
| 12 | 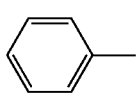 | 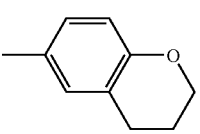 | H | 1 | CH—CH | 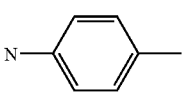 |
| 13 | 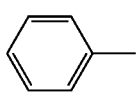 | 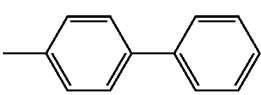 | H | 1 | CH—CH |  |
| 14 | 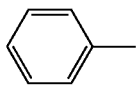 | 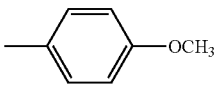 | H | 1 | CH—CH | 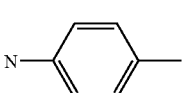 |
| 15 | 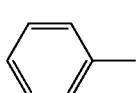 | 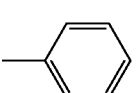 | H | 1 | CH—CH | 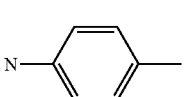 |
| 16 | 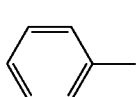 | 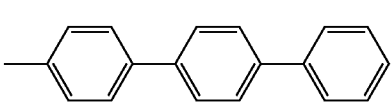 | H | 1 | CH—CH |  |

TABLE 1-continued
| 17 |  | 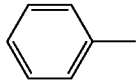 | H | 1 | CH—CH | 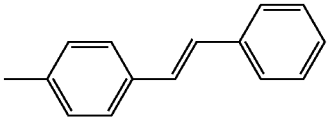 |
| Compound No. | Ar⁴ | Ar⁵ | Ar⁶ |
|---|---|---|---|
| 1 | H | 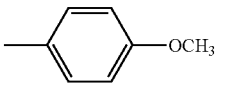 | —CH₃ |
| 2 | H | 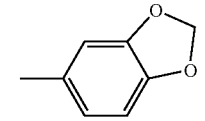 | —C₂H₅ |
| 3 | H | 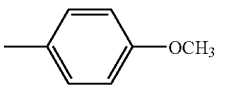 | H |
| 4 | H | 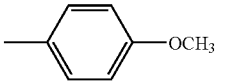 | H |
| 5 | H | 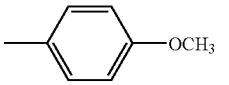 | H |
| 6 | H | 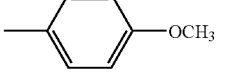 | H |
| 7 | —CH₃ | 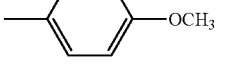 | H |
| 8 | H | 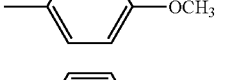 | H |
| 9 | —CH₃ | 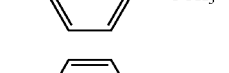 | H |
| 10 | —CH₃ | 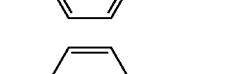 | H |
| 11 | H | 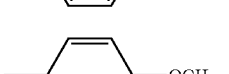 | H |
| 12 | H | 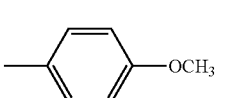 | H |
| 13 | H | 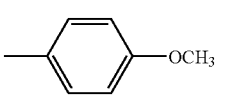 | H |
| 14 | H |  | H |

TABLE 1-continued

| | | | |
|---|---|---|---|
| 15 | (phenyl) | (4-methoxyphenyl) | H |
| 16 | —CH₃ | (4-methoxyphenyl) | —CH(CH₃)₂ |
| 17 | H | (4-methoxyphenyl) | —C₂H₅ |

TABLE 2

| Compound No. | N—Ar¹— | Ar² | R¹ | n | CR²—CR³ |
|---|---|---|---|---|---|
| 18 | N-(4-phenyl) | phenyl | —CH₃ | 2 | CH—CH |
| 19 | N-(3-methyl-4-phenyl) | phenyl | H | 1 | CH—CH |
| 20 | N-(3-ethyl-4-phenyl) | 4-methylphenyl | H | 1 | CH—CH |
| 21 | N-(3-isopropyl-4-phenyl) | 4-methylphenyl | H | 1 | CH—CH |
| 22 | N-(3-n-propyl-4-phenyl) | phenyl | H | 1 | CH—CH |
| 23 | N-(3-methyl-4-phenyl) | 4-methylphenyl | H | 1 | CH—CH |
| 24 | N-(3-methyl-4-phenyl) | 4-methylphenyl | H | 1 | CH—CH |
| 25 | N-(3-ethyl-4-phenyl) | 4-methylphenyl | H | 2 | CH—CH |

TABLE 2-continued

| No. | Ar¹ | Ar² | R | n | CH—CH |
|---|---|---|---|---|---|
| 26 | 3-CH(CH₃)₂, 4-CH₃ aniline (N-) | 4-CH₃-C₆H₄- | H | 1 | CH—CH |
| 27 | 3-n-C₃H₇, 4-CH₃ aniline (N-) | 4-CH₃-C₆H₄- | H | 1 | CH—CH |
| 28 | 4-CH₃-C₆H₄-N | C₆H₅- | H | 1 | CH—CH |
| 29 | 3-CH₃, 4-CH₃ aniline (N-) | 4-CH₃-C₆H₄- | H | 2 | CH—CH |
| 30 | 3-C₂H₅, 4-CH₃ aniline (N-) | 4-CH₃-C₆H₄- | H | 2 | CH—CH |
| 31 | 3-CH(CH₃)₂, 4-CH₃ aniline (N-) | 4-CH₃-C₆H₄- | H | 2 | CH—CH |
| 32 | 3-n-C₃H₇, 4-CH₃ aniline (N-) | 4-CH₃-C₆H₄- | H | 1 | CH—CH |
| 33 | 3-CH₃, 4-CH₃ aniline (N-) | C₆H₅- | H | 1 | CH—CH |
| 34 | 3-CH₃, 4-CH₃ aniline (N-) | C₆H₅- | H | 1 | CH—CH |

| Compound No. | Ar³ | Ar⁴ | Ar⁵ | Ar⁶ |
|---|---|---|---|---|
| 18 | C₆H₅- | H | 4-OCH₃-C₆H₄- | —CH₃ |
| 19 | 4-OCH₃-naphthyl | H | 4-N(CH₃)₂-C₆H₄- | 4-CH₃-C₆H₄- |

TABLE 2-continued
| 20 | 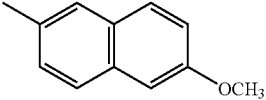 | H | 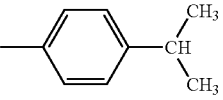 | —CH$_3$ |
| 21 | 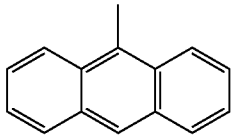 | H |  | H |
| 22 | 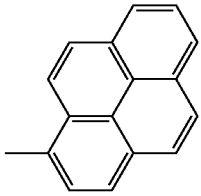 | H | 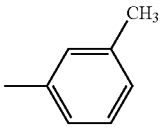 | H |
| 23 | 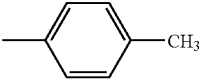 | 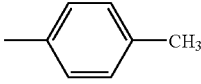 | 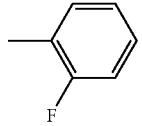 | H |
| 24 | 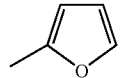 | —CH$_3$ | 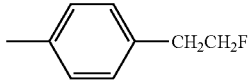 | 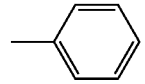 |
| 25 | 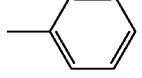 | H | 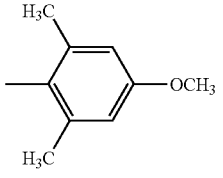 | 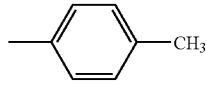 |
| 26 | 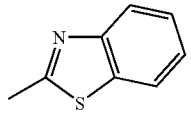 | H | 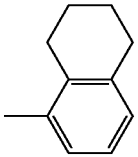 | 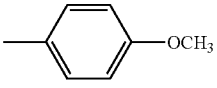 |
| 27 | 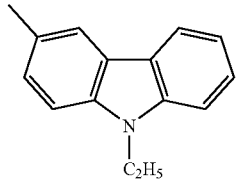 | H | 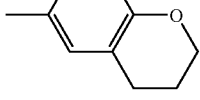 | 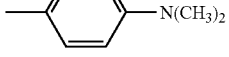 |
| 28 | 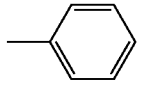 | H | 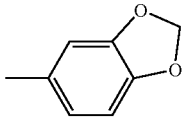 | H |
| 29 | 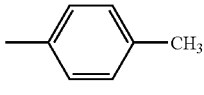 | 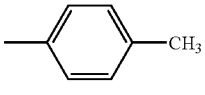 | 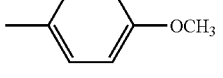 | 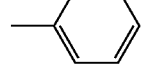 |
| 30 | 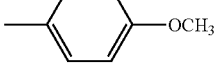 | 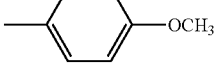 | 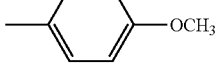 | H |

TABLE 2-continued

| No. | N—Ar¹— | Ar² | Ar³ | R¹ |
|---|---|---|---|---|
| 31 | -C₆H₄-N(CH₃)₂ (p) | -C₆H₄-N(CH₃)₂ (p) | -C₆H₄-OCH₃ (p) | H |
| 32 | -CH₂-C₆H₅ | -C₆H₅ | 2-furyl | H |
| 33 | 2-(5-ethyl)thienyl | -C₆H₅ | 4-methoxy-1-naphthyl | H |
| 34 | | 1-methylene-1,2,3,4-tetrahydronaphthyl | -C₆H₄-S-C₆H₅ (p) | —CH₃ |

TABLE 3

| Compound No. | N—Ar¹— | Ar² | R¹ | n | CR²—CR³ |
|---|---|---|---|---|---|
| 35 | 3-ethyl-4-methylanilino | -C₆H₅ | H | 1 | CH—CH |
| 36 | 3-isopropyl-4-methylanilino | -C₆H₄-CH₃ (p) | H | 1 | CH—CH |
| 37 | 3-n-propyl-4-methylanilino | -C₆H₅ | H | 1 | CH—CH |
| 38 | 3,4-dimethylanilino | -C₆H₄-CH₃ (p) | —CH₃ | 2 | CH—CH |
| 39 | 3,4-dimethylanilino | 1-naphthyl | —CH₃ | 1 | CH—CH |
| 40 | 3-ethyl-4-methylanilino | -C₆H₅ | -C₆H₅ | 1 | CH—CH |

TABLE 3-continued
| | | | | | |
|---|---|---|---|---|---|
| 41 | 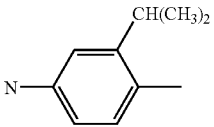 | 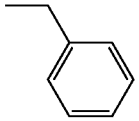 | H | 1 | CH—CH |
| 42 | 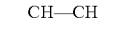 | 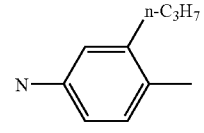 | H | 1 | 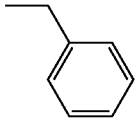 |
| 43 | 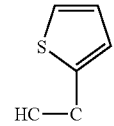 | 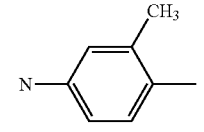 | H | 1 | 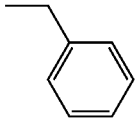 |
| 44 | 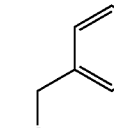 | 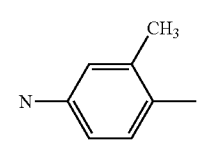 | H | 1 | 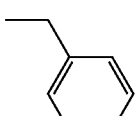 |
| 45 | 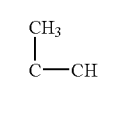 | 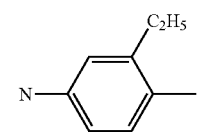 | 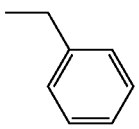 | 1 | 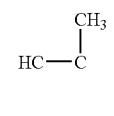 |
| 46 | 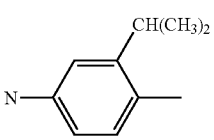 | 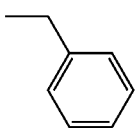 | H | 2 | 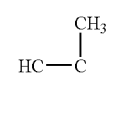 |
| 47 | 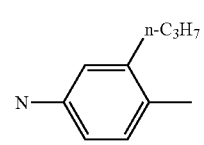 | 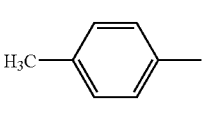 | H | 2 | 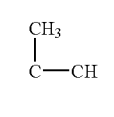 |
| 48 | 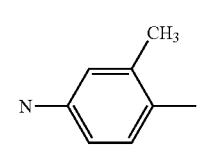 | 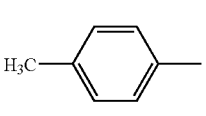 | H | 2 | 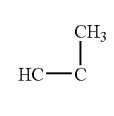 |
| 49 | 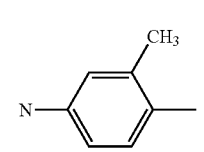 | 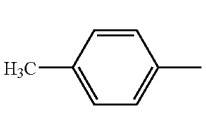 | H | 2 | 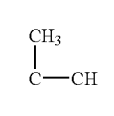 |
| 50 | 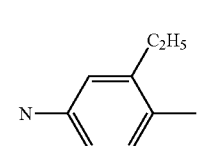 | 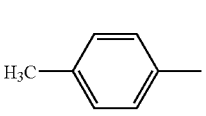 | H | 2 | 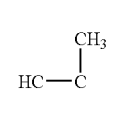 |
| 51 | 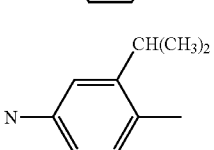 | 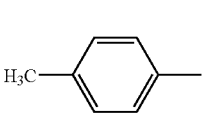 | H | 2 | 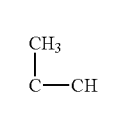 |

TABLE 3-continued

| Compound No. | Ar³ | Ar⁴ | Ar⁵ | Ar⁶ |
| --- | --- | --- | --- | --- |
| 35 | (9-methyleneanthracene) | | (phenyl) | —CH₃ |
| 36 | (5-methylenedibenzo[a,d]cycloheptene) | | (phenyl) | —CH₃ |
| 37 | (9-methylenethioxanthene) | | (phenyl) | —CH₃ |
| 38 | (phenyl) | H | (4-(dimethylamino)phenyl) —N(CH₃)₂ | H |
| 39 | (phenyl) | H | (benzothiazol-2-yl) | H |
| 40 | (phenyl) | H | (9-ethylcarbazol-3-yl) | H |
| 41 | (phenyl) | H | (phenyl) | H |
| 42 | (phenyl) | H | (4-methylphenyl) —CH₃ | H |
| 43 | (phenyl) | H | (4-methoxyphenyl) —OCH₃ | (furan-2-yl) |
| 44 | (phenyl) | H | (4-(dimethylamino)phenyl) —N(CH₃)₂ | (benzothiazol-2-yl) |
| 45 | (phenyl) | H | | (1-methylene-1,2,3,4-tetrahydronaphthalene) |

TABLE 3-continued
| | | | |
|---|---|---|---|
| 46 | 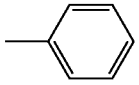 | H | 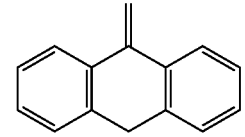 |
| 47 | 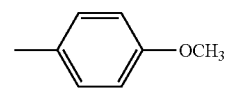 | H | 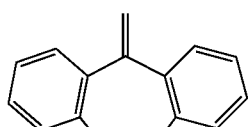 |
| 48 | 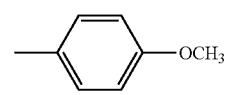 | —CH$_3$ | 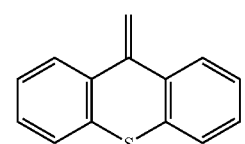 |
| 49 | 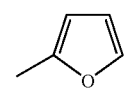 | —CH$_3$ | 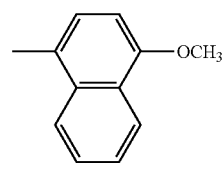 H |
| 50 | 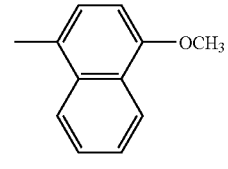 | —CH$_3$ | 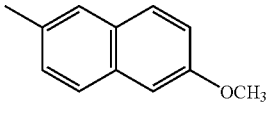 H |
| 51 | 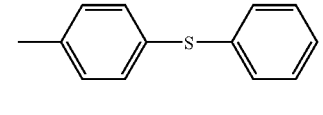 | —CH$_3$ | 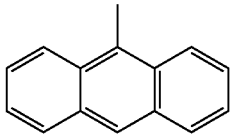 H |
TABLE 4
| Compound No. | N—Ar$^1$— | Ar$^2$ | R$^1$ | n | CR$^2$—CR$^3$ |
|---|---|---|---|---|---|
| 52 | 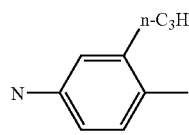 | 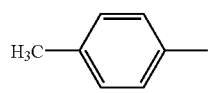 | H | 2 |  |
| 53 | 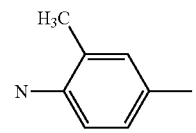 | 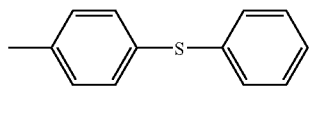 | H | 2 | 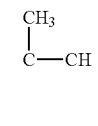 |
| 54 | 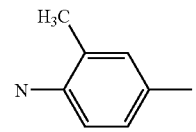 | 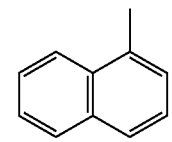 | H | 2 | 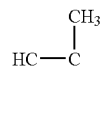 |
| 55 | 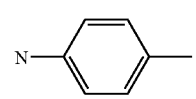 | 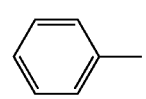 | H | 2 | CH—CH |

TABLE 4-continued

TABLE 4-continued

| 57 | 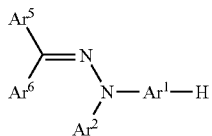 | H | (N-ethylcarbazol-3-yl) | H |
| 58 | 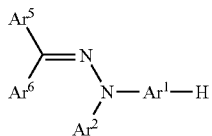 | H | 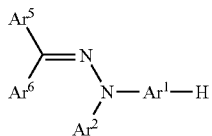 | H |
| 59 | 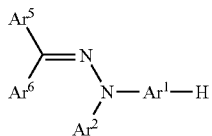 | H | 4-methylphenyl | H |
| 60 | 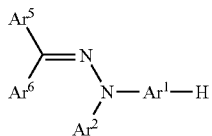 | H | 4-methoxyphenyl | H |

The hydrazone compounds of formula (1) of the invention may be produced through known reaction. For example, the compounds of formula (1) where $R^1$ is a hydrogen atom can be produced by formylating a hydrazone intermediate of a general formula (4):

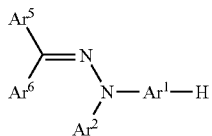

(4)

wherein $Ar^1$, $Ar^2$, $Ar^5$ and $Ar^6$ have the same meanings as in formula (1), to give a hydrazone-aldehyde intermediate of a general formula (5):

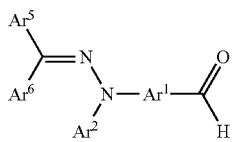

(5)

wherein $Ar^1$, $Ar^2$, $Ar^5$ and $Ar^6$ have the same meanings as in formula (1), followed by reacting the resulting hydrazone-aldehyde intermediate with a Witt reagent of a general formula (6):

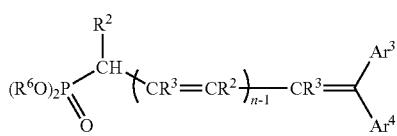

(6)

wherein $Ar^3$, $Ar^4$, $R^2$, $R^3$ and n have the same meanings as in formula (1), and $R^6$ represents a C1-3 alkyl group or an aryl group, under a basic condition.

The hydrazone intermediates of formula (4) may be produced, for example, by reacting a ketone compound of a general formula (4a):

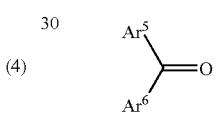

(4a)

wherein $Ar^5$ and $Ar^6$ have the same meanings as in formula (1), with a hydrazine compound of a general formula (4b):

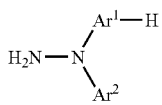

(4b)

wherein $Ar^1$ and $Ar^2$ have the same meanings as in formula (1), for dehydrating condensation. The reaction for dehydrating condensation goes on almost quantitatively by heating the ketone compound of formula (4a) and the hydrazine compound of formula (4b) in an alcoholic solvent in the presence of an acid catalyst. The reaction temperature and the reaction time for the hydrating condensation reaction are not specifically defined, and may be suitably selected depending on various conditions such as the type and the amount of the ketone compound and the hydrazine compound used. Preferably, however, the reaction temperature is from 70 to 80° C. and the reaction time is from 4 to 8 hours. The alcoholic solvent for the dehydrating condensation includes ethanol, butanol, and isopropanol. The acid catalyst includes p-toluenesulfonic acid, camphorsulfonic acid, and acetic acid. The amount of the acid catalyst to be used not specifically defined, may be, for example, from 0.001 to 0.01 mol equivalents to 1.0 mol equivalent of the ketone compound of formula (4a).

For example, hydrazone intermediates of formula (4) where $Ar^1$ is a phenylene group, $Ar^2$ and $Ar^5$ are a phenyl group and $Ar^6$ is a methyl group may be produced by using acetophenone as the ketone compound of formula (4a) and N,N-diphenylhydrazine as the hydrazine compound of formula (4b).

The formylation of hydrazone intermediates of formula (4) may be effected, for example, in any mode of known formulation such as Vilsmeier formulation.

The Vilsmeier formulation of the hydrazone intermediate of formula (4) may be effected, for example, as follows: First, phosphorus oxychloride, and N,N-dimethylformamide (DMF), N-methyl-N-phenylformamide or N, N-diphenylformamide are added to a suitable solvent, to prepare a Vilsmeier reagent. The usable solvent may be an aprotic non-polar solvent such as N,N-dimethylformamide, a halogenohydrocarbon such as 1,2-dichloroethane, or an aromatic hydrocarbon such as toluene.

Next, 1.0 mol equivalent of the hydrazone intermediate of formula (4) is added to from 1.0 to 1:3 mol equivalents of the thus-prepared Vilsmeier reagent and reacted under heat at 80 to 100° C. for 2 to 8 hours with stirring. After the reaction, the system is hydrolyzed with an aqueous alkali solution to obtain a hydrazone-aldehyde intermediate of formula (5). The aqueous alkali solution to be used for the hydrolysis may be an aqueous solution of 1 to 8 N sodium hydroxide or potassium hydroxide. In the manner as above, the hydrazone-aldehyde intermediate of formula (5) may be produced at a high yield.

The Wittig reagent of formula (6) with which the hydrazone-aldehyde intermediate of formula (5) is reacted may be produced, for example, by mixing a phosphite compound of a general formula (6a):

(6a)

wherein $R^6$ has the same meaning as in formula (6), with an allyl halide compound of a general formula (6b):

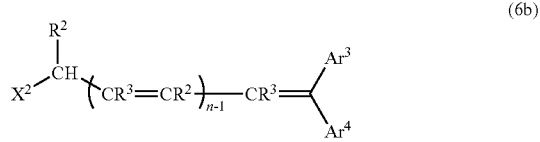

(6b)

wherein $Ar^3$, $Ar^4$, $R^2$, $R^3$ and n have the same meanings as in formula (1), and $X^2$ represents a halogen atom, almost in a ratio of 1/1 by mol in the absence of a solvent, and reacted with stirring under heat.

The phosphite compound of formula (6a) includes trialkyl phosphites such as triethyl phosphite, and triisopropyl phosphite; and triaryl phosphites such as triphenyl phosphite. In the allyl halide compound of formula (6b), $X^2$ may be a fluorine atom, a chlorine atom, a bromine atom or an iodine atom. Preferred is the compound of formula (6b) where $X^2$ is a chlorine atom or a bromine atom.

The Wittig-Horner reaction of the hydrazone-aldehyde intermediate of formula (5) with the Wittig reagent of formula (6) may be effected, for example, as follows: First, 1.0 mol equivalent of a hydrazone-aldehyde intermediate of formula (5), from 1.0 to 1.2 mol equivalents of a Wittig reagent of formula (6), and from 1.0 to 1.3 mol equivalents of a metal alkoxide base are added to a suitable solvent, and reacted with stirring at room temperature (20 to 30° C.) or under heat at 30 to 60° C. for 2 to 8 hours. This gives a hydrazone compound of formula (1) of the invention where $R^1$ is a hydrogen at a high yield.

The solvent used in the Wittig-Horner reaction may be an aromatic hydrocarbon such as toluene, and xylene; an ether such as diethyl ether, tetrahydrofuran (THF), and ethylene glycol dimethyl ether; or an aprotic non-polar solvent such as N,N-dimethylformamide, and dimethylsulfoxide. The metal alkoxide base includes potassium t-butoxide, sodium ethoxide, and sodium methoxide.

Compounds of formula (1) where $R^1$ is a group except hydrogen atom may be produced, for example, by acylating a hydrazone intermediate of formula (4) mentioned above to give hydrazone-ketone intermediate of a general formula (7):

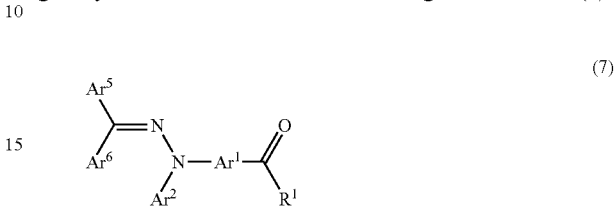

(7)

wherein $Ar^1$, $Ar^2$, $Ar^5$, $Ar^6$ and $R^1$ have the same meanings as in formula (1), but $R^1$ is not a hydrogen atom, followed by reacting the resulting hydrazone-ketone intermediate with a Grignard reagent that is obtained by treating an allyl halide compound of formula (6b) mentioned above with a metal magnesium.

The acylation of the hydrazone intermediate of formula (4) may be effected in any mode of known acylation such as Friedel-Craft acylation. When Friedel-Craft acylation is employed, for example, a hydrazone intermediate of formula (4) may be reacted with an acyl halide compound of a general formula (7a):

(7a)

wherein $R^1$ has the same meaning as in formula (1), but $R^1$ is not a hydrogen atom, and X1 represents a halogen atom, or a carboxylic acid anhydride of a general formula (7b):

(7b)

wherein $R^1$ has the same meaning as in formula (1), but $R^1$ is not a hydrogen atom, in the presence of a Lewis acid to produce a hydrazone-ketone intermediate of formula (7).

The Friedel-Craft acylation of the hydrazone intermediate of formula (4) may be effected, for example, as follows: First, a Lewis acid, and an acyl halide compound of formula (7a) or a carboxylic acid anhydride of formula (7b) are added to a suitable solvent and stirred for 0.5 to 1 hour to prepare a Friedel-Craft reagent. The usable solvent may be a halogenohydrocarbon such as chloroform, and 1,2-dichloromethane; or an aromatic hydrocarbon such as nitrobenzene. The Lewis acid includes aluminium chloride, tin chloride, and zinc chloride. The amount of the Lewis acid to be used may be, for example, from 0.8 to 1.3 mol equivalents, preferably from 1.0 to 1.2 mol equivalents to 1.0 mol equivalent of the acyl halide of formula (5a); or it may be, for example, from 2.0 to 2.2 mol equivalents to 1.0 mol equivalent of the carboxylic acid anhydride of formula (5b).

Next, 1.0 mol equivalent of the hydrazone intermediate of formula (4) is added to from 1.0 to 1.2 mol equivalents of the thus-prepared Friedel-Craft acylation reagent, and the reaction solution is stirred for 2 to 8 hours while kept at −40° C. to 30° C. After the reaction, this is hydrolyzed with an aqueous alkali solution to obtain a hydrazone-ketone intermediate of formula (7). This is hydrolyzed with an aqueous 1 to 8 N alkali solution. The aqueous alkali solution to be used for the hydrolysis is an aqueous 1 to 8 N sodium hydroxide or potassium hydroxide solution. In that manner, a hydrazone-ketone intermediate of formula (7) can be obtained at a high yield.

The Grignard reaction between the hydrazone-ketone intermediate of formula (7) with the above Grignard reagent may be effected, for example, as follows: First, an allyl halide compound of formula (6b) and a metal magnesium are added to a suitable solvent in a ratio of nearly 1/1 by mol to prepare a Grignard reagent. The solvent for use herein may be an aromatic hydrocarbon such as toluene, and xylene; or an ether such as diethyl ether, tetrahydrofuran (THF), and ethylene glycol dimethyl ether. Preferably, the solvent is dewatered with a metal sodium before used herein.

1.0 mol equivalent of the hydrazone-ketone intermediate of formula (7) is added to from 1.1 to 1.2 mol equivalents of the thus-prepared Grignard reagent with cooling, and then stirred at room temperature (e.g., 20 to 30° C.) or under heat at 30° C. to 60° C. for 2 to 8 hours. In that manner, hydrazone compounds of formula (1) of the invention where $R^1$ is a substituent except hydrogen can be obtained at a high yield.

The hydrazone compound of formula (1) of the invention, produced in the manner as above, may be readily isolated and purified from the reaction mixture in any ordinary separation method of, for example, solvent extraction, recrystallization or column chromatography, and it may be obtained as a product of high purity.

The electrophotographic photoreceptor (hereinafter it may be simply referred to as "photoreceptor") of the invention comprises the hydrazone compound of formula (1) of the invention mentioned hereinabove, as the charge transporting substance therein, and it includes various embodiments. These are described in detail hereinunder with reference to the drawings.

FIG. 1 is a fragmentary cross sectional view schematically showing the constitution of an electrophotographic photoreceptor 1 as a first embodiment of electrophotographic photoreceptor according to the invention. The electrophotographic photoreceptor 1 includes a sheet-like conductive substrate 11 formed of a conductive material, a charge generating layer 12 containing a charge generating substance and laminated on the conductive substrate 11, and a charge transporting layer 13 containing a charge transporting substance and further laminated on the charge generating layer 12. The charge generating layer 12 and the charge transporting layer 13 form a laminate-structured photosensitive layer 14, a type of a photosensitive layer 10. Accordingly, the photoreceptor 1 is a laminate-structured photoreceptor.

The conductive substrate 11 functions as an electrode of the photoreceptor 1 and also as a supporting member for the layers 12, 13. The shape of the conductive substrate 11 is a sheet in this embodiment. However, not limited to it, the support may be columnar or cylindrical or may also be in the form of an endless belt.

The conductive materials constituting the conductive substrate 11 can include, for example, metal element such as aluminum, copper, zinc, titanium, etc., and an alloy such as an aluminum alloy and stainless steel, etc. It is not limited to those metal materials, but those prepared by laminating a metal foil, vapor depositing a metal material or vapor depositing or coating a layer of a conductive compound such as conductive polymers, tin oxide, indium oxide, etc., on the surface of polymeric materials such as polyethylene terephthalate, nylon or polystyrene, etc., hard paper, or glass may also be used. Such conductive materials are used while being formed into a predetermined shape.

The surface of the conductive substrate 11 may optionally be subjected to an anodizing coating film treatment, a surface treatment with a chemical or hot water, etc. a coloring treatment, or a random reflection treatment such as of surface roughening within a range of giving no effects on the picture quality. In an electrophotographic process using a laser as a light source for exposure, since the wavelength of the laser light is uniform, the laser light reflected on the surface of the photoreceptor and the laser light reflected in the inside of the photoreceptor cause interference, and interference fringes caused by the interference sometimes appear on the image to cause image defects. The image defects caused by the interference of the coherent laser light with uniform wavelength can be prevented by applying the treatment described above to the surface of the conductive substrate 11.

The charge generating layer 12 provided on the conductive substrate 11 contains a charge generating substance that generates a charge through absorption of light. Substances effective for the charge generating substance are organic photoconductive materials, for example, azo pigments such as monoazo pigments, bisazo pigments, and trisazo pigments; indigo pigments such as indigo, and thioindigo; perylene pigments such as perylenimide, and perylenic acid anhydride; polycyclic quinone pigments such as anthraquinone, and pyrenequinone; phthalocyanine compounds including metal phthalocyanines such as oxotitanium phthalocyanine compounds and metal-free phthalocyanines; squarylium dyes, pyrylium salts and thiopyrylium salts, triphenylmethane dyes; as well as inorganic photoconductive materials such as selenium and amorphous silicon. One or more of these charge generating substances may be used herein either singly or as combined.

Of those charge generating substances, preferred for use herein are phthalocyanine compounds, especially oxotitanium phthalocyanine compounds. Oxotitanium phthalocyanine compounds as referred to herein include oxotitanium phthalocyanine and its derivatives. Oxotitanium phthalocyanine derivatives include those derived from oxotitanium phthalocyanine by substituting the hydrogen atom of the aromatic ring in the phthalocyanine group of the compound with a substituent, for example, a halogen atom such as chlorine atom or fluorine atom, or a nitro group, a cyano group or a sulfonic acid group; and those derived from oxotitanium phthalocyanine in which the center metal, titanium atom is coordinated with a ligand such as a chlorine atom.

Using an oxotitanium phthalocyanine compound as the charge generating substance realizes a photoreceptor 1 having good sensitivity and resolution. It may be presumed that the reason for it would be because the combination of the oxotitanium phthalocyanine compound and the hydrazone compound of formula (1) of the invention that is contained in the charge transporting layer 13 as the charge transporting substance therein may be good. Specifically, the oxotitanium phthalocyanine compound has good charge generating capability and charge-injecting capability, and when it has absorbed light, it generates a lot of charges and, not accumulating the thus-generated charges inside it, it efficiently injects the charges into the hydrazone compound of the invention contained in the charge transporting layer. Further, since the hydrazone compound of the invention has excellent charge transporting capability, it may smoothly transport the charges injected thereinto from the oxotitanium phthalocyanine compound, to the surface of the photosensitive layer 14. Accordingly, combining the hydrazone compound of formula (1) of the invention with an oxotitanium phthalocyanine compound realizes good sensitivity and good resolution.

It is desirable that the oxotitanium phthalocyanine compound for use herein has a specific crystal structure. Preferably, the oxotitanium phthalocyanine compound for use herein has a crystal structure that shows a diffraction peak at least at a Bragg angle 2θ (error: 2θ±0.20) of 27.2° in the X-ray diffraction spectrum thereof to a Cu—Kα characteristic X ray (wavelength: 1.54 angstroms). The Bragg angle 2θ as referred to herein means the angle formed by an incident X ray and a diffracted X ray, and it is a diffraction angle.

The oxotitanium phthalocyanine compound can be produced by a production process known so far, such as a process described in "Phthalocyanine Compounds" written by Moser and Thomas. For example, an oxotitanium phthalocyanine can be obtained by heat-melting phthalonitrile and titanium tetrachloride, or by reacting them under heating in an appropriate solvent such as α-chloronaphthalene to synthesize a dichlorotitanium phthalocyanine, and then hydrolyzing the same with a base or water. Further, the oxotitanium phthalocyanine can also be produced by reacting isoindoline and titanium tetraalkoxide such as tetrabuthoxy titanium in an appropriate solvent such as an N-methyl pyrrolidone.

The charge generating substance may also be used in combination with sensitizing dyes, for example, triphenylmethane series dyes typically represented by methyl violet, crystal violet, night blue and Victoria blue; acrydine dyes represented by erythrocine, Rhodamine B, Rhodamine 3R, acrydine orange and flapeocine, etc; thiazine dyes typically represented by methylene blue and methylene green; oxazine dyes typically represented by capriblue, meldolablue; cyanine dye; styryl dye; pyrylium salt dye; or thiopyrylium salt dye.

The charge generating layer 12 may contain a binder resin for improving the bindability thereof. The binder resin for use in the charge generating layer 12 includes, for example, polyester resins, polystyrene resins, polyurethane resins, phenolic resins, alkyd resins, melamine resins, epoxy resins, silicone resins, acrylic resins, methacrylic resins, polycarbonate resins, polyarylate resins, phenoxy resins, polyvinylbutyral resins, polyvinylformal resins and other resins; as well as copolymer resins containing two or more repetitive units of these resins. Specific examples of the copolymer resins are insulating resins such as vinyl chloride-vinyl acetate copolymer resins, vinyl chloride-vinyl acetate-maleic anhydride copolymer resins, and acrylonitrile-styrene copolymer resins. The binder resin for use herein is not limited to these, and any and every binder resin generally used in the art is usable herein. One or more binder resins may be used herein either singly or as combined.

The ratio of the charge generating substance to be in the charge generating layer 12 is preferably from 10% by weight to 99% by weight. If the ratio of the charge generating substance is smaller than 10% by weight, then the sensitivity of the photoreceptor 1 may lower. If the ratio of the charge generating substance is larger than 99% by weight, then the film strength of the charge generating layer 12 may lower. If so, in addition, the dispersibility of the charge generating substance in the charge generating layer 12 may lower and coarse particles may increase in the layer, and, as a result, the surface charges not in the area where the charges are to be erased may decrease through exposure to light, and image defects, especially image fogs referred to as black spots formed by toner adhesion to a white background area may thereby increase.

For forming the charge generating layer 12, for example, employable is a vacuum evaporation method of depositing the charge generating substance as above on the surface of the conductive substrate 11 in a mode of vacuum deposition, or a coating method of applying a charge generating layer-forming coating liquid, which contains the charge generating substance as above, onto the surface of the conductive substrate 11. Of the two, the coating method is preferred. The charge generating layer-forming coating liquid may be prepared, for example, by adding the charge generating substance as above and optionally the binder resin as above to a suitable solvent followed by dispersing them according to a known method.

The solvents used for the coating solution for use in the charge generating layer include, for example, halogenated hydrocarbons such as dichloromethane and dichloroethane; ketones such as acetone, methyl ethyl ketone, cyclohexanone; esters such as ethyl acetate and butyl acetate; ethers such as tetrahydrofuran and dioxane; alkylethers of ethylene glycol such as 1,2-dimethoxyethane; aromatic hydrocarbons such as benzene, toluene and xylene; and aprotic polar solvents such as N,N-dimethylformamide and N,N-dimethyl acetoamide. The solvents may be used alone or two or more of them may also be mixed and used as a mixed solvent.

The charge generating substance may previously be pulverized by a pulverizer before dispersion into the solution. The pulverizer used for the pulverization can include, for example, a ball mill, a sand mill, an attritor, a vibration mill and a supersonic dispersing machine.

The dispersing machine used for dispersing the charge generating substance into the solution can include, for example, a paint shaker, a ball mill and a sand mill. As the dispersion conditions in this case, appropriate conditions are selected such that intrusion of impurities due to abrasion of a container to be used and members constituting the dispersing machine does not occur.

The coating method of the coating solution for use in charge generating layer can include, for example, a spraying method, a bar coating method, a roll coating method, a blade method, a wringing method and a dip coating method. Among the coating methods described above, the dip coating method, in particular, is a method of dipping a substrate into a coating tank filled with the coating solution and then pulling it up at a constant speed or at a gradually changing speed thereby forming a layer on the surface of a substrate. Since this is relatively simple and excellent in view of the productivity and the cost, it is used suitably. For stabilizing the dispersibility of the coating solution, a coating solution dispersing device typically represented by a supersonic generation device may also be provided to the apparatus used for the dip coating method. The coating method is not restricted to them but an optimal method can be selected appropriately while taking the physical property of the coating solution and the productivity into consideration.

The thickness of the charge generating layer 12 is, preferably, 0.05 μm or more and 5 μm or less and, more preferably, 0.1 μm or more and 1 μm or less. In a case where the thickness of the charge generating layer 12 is less than 0.05 μm, the efficiency of light absorption is lowered to possibly lower the sensitivity of the photoreceptor 1. In a case where the thickness of the charge generating layer 12 exceeds 5 μm, the movement of the charges in the charge generating layer 12 constitutes a rate determining step in the process of eliminating the charges on the surface of the photosensitive layer 14 to possibly lower the sensitivity of the photoreceptor 1.

The charge transporting layer 13 provided on the charge generating layer 12 is constituted to contain a charge transporting substance having the ability to accept the charges that have been generated by the charge generating substance contained in the charge generating layer 12 and to transport them, and a binder resin for binding the charge transporting substance. For the charge transporting substance, used is the hydrazone compound of formula (1) of the invention.

As so mentioned hereinabove, the hydrazone compound of formula (1) of the invention has excellent charge transporting capability, especially excellent hole-transporting capability, and therefore using the hydrazone compound of formula (1) of the invention as a charge transporting substance realizes a photoreceptor 1 of high reliability having good electric properties such as good chargeability, sensitivity and light responsibility, and having good electric durability and environment stability. Even though the photoreceptor 1 is exposed to external light during its maintenance, the good electric properties intrinsic to the photoreceptor 1 are not worsened.

As the hydrazone compound of formula (1), one or more selected from the group consisting of Compounds Nos. 1 to 60 shown in Table 1 to Table 4 mentioned above may be used either singly or as combined.

For the binder resin constituting the charge transporting layer 13, those excellent in compatibility with the hydrazone compound of the invention represented by the general formula (1) are selected. Specific examples include, for example, polymethyl methacrylate resin, polystyrene resin; vinyl polymer resins such as polyvinyl chloride resin; and copolymer resins containing two or more of repetitive units constituting them, as well as polycarbonate resin, polyester resin, polyester carbonate resin, polysulfone resin, phenoxy resin, epoxy resin, silicone resin, polyarylate resin, polyamide resin, polyether resin, polyurethane resin, polyacrylamide resin and phenol resin. Further, thermosetting resins formed by partially cross-linking the resins described above may also be included. The resins may be used alone or two or more of the resins may be used in admixture. Among the resins described above, polystyrene resin, polycarbonate resin, polyarylate resin, or polyphenylene oxide can be used suitably since it has a volume resistivity of $10^{13}$ Ω·cm or more, and excellent electrical insulative property and is also excellent in the film-forming property and the potential characteristic.

In the charge transporting layer 13, the ratio of the weight (B) of the binder resin to the weight (A) of the hydrazone compound of formula (1), B/A is preferably from 1.2 to 3.0. When the ratio B/A is 1.2 or more so that the binder resin could be in the charge transporting layer in a high ratio, then the printing durability of the charge transporting layer 13 may be increased.

However, when the ratio of the binder resin is increased in that manner, then the ratio of the hydrazone compound of formula (1) to be in the layer as the charge transporting substance therein decreases. When a conventional known charge transporting substance is used and when the ratio of the weight of the binder resin to the weight of the charge transporting substance in the charge transporting layer 13 (binder resin/charge transporting substance) is at least 1.2 like in the invention, then the light responsibility of the photoreceptor will be unsatisfactory and image defects may occur. As opposed to this, since the hydrazone compound of formula (1) has especially excellent charge transporting capability, the photoreceptor 1 containing it may still have a sufficiently high light responsibility and can provide high-quality images even though the ratio B/A is at least 1.2 and the ratio of the binder resin in the charge transporting layer 13 is increased. Accordingly, in the photoreceptor 1, the ratio B/A may be at least 1.2, whereby the printing durability of the charge transporting layer 13 may be increased and the mechanical durability thereof may also be increased not lowering the light responsibility of the photoreceptor 1.

If the ratio B/A is larger than 3.0, then the ratio of the binder resin may be too high and the sensitivity of the photoreceptor 1 may lower. When the charge transporting layer 13 is formed according to a dipping method and when the ratio B/A is larger than 3.0, then the viscosity of the coating liquid increases and the coating speed may lower and, as a result, the producibility of the photoreceptor may significantly lower. When the amount of the solvent in the coating liquid is increased so as to prevent the viscosity of the coating liquid from increasing, then a brushing phenomenon may occur and the charge transporting layer 13 formed may be whitish and cloudy. In addition, when the ratio B/A is smaller than 1.2, then the ratio of the binder resin will be too low, and the printing durability of the charge transporting layer 13 may lower, and as a result, the wear loss of the photosensitive layer 14 may increase and the chargeability of the photoreceptor 1 may therefore decrease.

The charge transporting layer 13 may contain any other charge transporting substance except the hydrazone compound of formula (1) of the invention, as long as not detracting from the good characteristics of the invention. The charge transporting substance that may be combined with the hydrazone compound of formula (1) includes enamine compounds such as enamine-styryl derivatives, enamine-hydrazone derivatives, enamine-butadiene derivatives, and enamine-hexatriene derivatives; and carbazole derivatives, oxazole derivatives, oxadiazole derivatives, thiazole derivatives, thiadiazole derivatives, triazole derivatives, imidazole derivatives, imidazolone derivatives, imidazolidine derivatives, bisimidazolidine derivatives, hydrazone compounds except those of formula (1), styryl compounds, polycyclic aromatic compounds, indole derivatives, pyrazoline derivatives, oxazolone derivatives, benzimidazole derivatives, quinazoline derivatives, benzofuran derivatives, acridine derivatives, phenazine derivatives, aminostilbene derivatives, triarylamine derivatives, triarylmethane derivatives, phenylenediamine derivatives, stilbene derivatives, and benzidine derivatives. In addition, further mentioned are polymers having a group derived from these compounds as the backbone chain or side chains thereof, such as poly(N-vinylcarbazole), poly (1-vinylpyrene) and poly(9-vinylanthracene).

To the charge transporting layer 13, various additives may be added such as plasticizer, leveling agent, or fine particles of inorganic compound or organic compound, as long as not detracting from the good characteristics of the invention. Adding a plasticizer or a leveling agent thereto improves the film formability, the elasticity and the smoothness of the charge transporting layer 13. Adding fine particles of inorganic compound or organic compound thereto enhances the mechanical strength of the charge transporting layer 13 and improves the electric properties thereof. The plasticizer includes, for example, dibasic acid esters such as phthalates, and fatty acid esters, phosphates, chloroparaffin and epoxy-type plasticizer. The leveling agent is, for example, a silicone-type leveling agent.

Like in the case of forming the charge generating layer 12 according to a coating method as above, the charge transporting layer may be formed, for example, by applying a charge transporting layer-forming coating liquid that contains the hydrazone compound of formula (1) and the binder resin as above, onto the charge generating layer 12. The charge transporting layer-forming coating liquid may be prepared, for example, by adding a hydrazone compound of formula (1) and a binder resin and optionally any other charge transporting substance than the hydrazone compound of formula (1) and additives as above, to a suitable solvent, and dissolving or dispersing them.

The solvent to be used for the coating solution for use in charge transporting layer can include, for example, aromatic hydrocarbons such as benzene, toluene, xylene, and monochlorobenzene; halogenated hydrocarbons such as dichloromethane and dichloroethane; ethers such as tetrahydrofuran, dioxane and dimethoxymethyl ether; and aprotic polar solvents such as N,N-dimethyl formamide. The solvents may be used alone or two or more of them may be used in admixture. Further, solvents such as alcohols, acetonitrile or methyl ethyl ketone may be further added and used to the solvent described above.

The coating method for the coating solution for use in charge transporting layer can include, for example, a spraying method, bar coating method, roll coating method, blade method, wringing method, and dip coating method. Among the coating methods described above, since dip coating method is excellent, particularly, in various points of view as described above, it is used suitably also in a case of forming the charge transporting layer 13.

The thickness of the charge transporting layer 13 is, preferably, 5 µm or more and 50 µm or less, and more preferably, 10 µm or more and 40 µm or less. In a case where the thickness of the charge transporting layer 13 is less than 5 µm, the charge retainability on the surface of the photoreceptor may possibly be lowered. In a case where the thickness of the charge transporting layer 13 exceeds 50 µm, the resolution power of the photoreceptor 1 may possibly be lowered.

The photosensitive layer 14 has a laminated structure in which the charge generating layer 12 and the charge transporting layer 13 formed as described above are laminated. By sharing the charge generating function and the charge transporting function to respective layers, materials constituting the respective layers can be selected independently so that materials optimal to the charge generating function and the charge transporting function can be selected respectively. Accordingly, the photoreceptor 1 is excellent, particularly, in the electric characteristics such as the chargeability, the sensitivity and the light responsiveness, as well as in electrical and mechanical durabilities.

One or more of sensitizers such as an electron accepting material and a dye may be added to each of the layers of the photosensitive layer 14, that is, the charge generating layer 12 and the charge transporting layer 13 within such a range as not deteriorating the preferable characteristics of the invention. By the addition of the sensitizer, the sensitivity of the photoreceptor 1 is improved and, further, rise of the residual potential and fatigue due to repetitive use can be restricted to improve the electrical durability.

As the electron accepting material, there can be used electron attracting materials, for example: acid anhydrides such as succinic acid anhydride, maleic acid anhydride, phthalic acid anhydride and 4-chloronaphthalic acid anhydride; cyano compounds such as tetracyanoethylene and terephthal malone dinitrile; aldehydes such as 4-nitrobenzaldehyde; anthraquinones such as anthraquinone and 1-nitroanthraquinone; polycyclic or heterocyclic nitro compounds such as 2,4,7-trinitrofluolenone and 2,4,5,7-tetranitrofluorenone or a diphenoquinone compound. Further, the electron attracting materials described above formed into polymeric materials can also be used.

As the dye, for example, xantene series dyes, thiadine dyes, triphenylmethane dyes, quinoline series pigments or organic photoconductive compounds such as copper phthalocyanine can be used. Such organic photoconductive compounds function as an optical sensitizer.

Further, an antioxidant or UV-absorbent, etc. may also be added to each of the layers 12 and 13 of the photosensitive layer 14. Particularly, it is preferable to add the anti-oxidant, UV-absorbent, etc. to the charge transporting layer 13. By the addition of the anti-oxidant or the UV-absorbent to each of the layers 12, 13 of the photosensitive layer 14, preferably, to the charge transporting layer 13, the potential characteristics of the photoreceptor 1 can be improved. Further, this can improve the stability of the coating solution in forming each of the layers by coating. Further, this makes it possible to mitigate the wear deterioration due to repetitive use of the photoreceptor 1 to improve the electrical durability.

As the antioxidant, phenol series compounds, hydroquinone series compounds, tocopherol series compounds or amine series compounds etc. can be used. Among them, hindered phenol derivatives, hindered amine derivatives or a mixture thereof are used suitably. The antioxidant is used within a range, preferably, of 0.1 parts by weight or more and 50 parts by weight or less based on 100 parts by weight of the charge transporting substance. In a case where the amount of the anti-oxidant relative to be used based on 100 parts by weight of the charge transporting substance is less than 0.1 parts by weight, the effect of improving the stability of the coating solution and the electric durability of the photoreceptor can not possibly be provided sufficiently. On the other hand, in a case where it exceeds 50 parts by weight, undesired effects may possibly be given on the characteristics of the photoreceptor.

FIG. 2 is a fragmentary cross sectional view schematically showing the constitution of an electrophotographic photoreceptor 2 as a second embodiment of an electrophotographic photoreceptor according to the invention. The electrophotographic photoreceptor 2 of this embodiment is similar to the electrophotographic photoreceptor 1 of the first embodiment shown in FIG. 1 in which corresponding portions carry identical reference numerals for which descriptions are to be omitted.

What is to be noted in the electrophotographic photoreceptor 2 is that an intermediate layer 15 is disposed between a conductive substrate 11 and a photosensitive layer 14.

In a case where the intermediate layer 15 is not present between the conductive substrate 11 and the photosensitive layer 14, charges are injected from the conductive substrate 11 to the photosensitive layer 14 to lower the chargeability of the photosensitive layer 14 and decrease the surface charges in the portions other than those to be exposed to sometimes result in defects such as fogging in images. Particularly, in a case of forming images by using a reversal development process, since a toner is deposited to a portion where the surface charges are decreased by exposure to form toner images, when the surface charges are decreased by other factors than exposure, image fogging referred to as the black spots which are fine black spots formed by the toner deposited on the white background occur to possibly result in remarkable degradation of the picture quality. As described above, in a case where the intermediate layer 15 is not present between the conductive substrate 11 and the photosensitive layer 14, lowering of the chargeability occurs in the fine region due to the defects of the conductive substrate 11 or the photosensitive layer 14 to cause image fogging such as black spots to possibly form remarkable image defects.

In the photosensitive body 2 of this embodiment, since the intermediate layer 15 is provided between the conductive substrate 11 and the photosensitive layer 14 as described above, injection of charges from the conductive substrate 11 to the photosensitive layer 14 can be prevented. Accordingly, lowering of the chargeability of the photosensitive layer 14 can be prevented, and decrease of the surface charges in the portions other than the exposed portion can be suppressed to prevent occurrence of defects such as fogging in the images.

Further, by the provision of the intermediate layer 15, the defects on the surface of the conductive substrate 11 can be covered to obtain a uniform surface so that the film-forming property of photosensitive layer 14 can be improved. Further, since the intermediate layer 15 functions as an adhesive for adhering the conductive substrate 11 and the photosensitive layer 14, peeling of the photosensitive layer 14 from the conductive substrate 11 can be suppressed.

When the intermediate layer 15 is provided between the conductive substrate 11 and the photosensitive layer 14, then the sensitivity of the photoreceptor may lower. However, since the photosensitive layer 14 of the photoreceptor 2 contains a hydrazone compound of the invention having excellent charge transporting capability, the sensitivity of the photoreceptor 2 does not lower even though the intermediate layer 15 is provided. Specifically, in the photoreceptor 2 of the invention, the intermediate layer 15 may be provided without lowering the sensitivity thereof.

For the intermediate layer 15, a resin layer comprising various kinds of resin materials or an alumite layer is used.

The resin material constituting the resin layer can include, for example, synthetic resins such as polyethylene resin, polypropylene resin, polystyrene resin, acrylic resin, vinyl chloride resin, vinyl acetate resin, polyurethane resin, epoxy resin, polyester resin, melamine resin, silicone resin, polyvinyl butyral resin and polyamide resin, as well as copolymer resins containing two or more of repetitive units constituting the synthesis resins. Further, it may also include casein, gelatin, polyvinyl alcohol and ethyl cellulose. Among the resins, use of the polyamide resin is preferable and, particularly, alcohol soluble nylon resin is used preferably. The preferable alcohol soluble nylon resin can include so-called a copolymerized nylon formed by co polymerizing, for example, 6-nylon, 6,6-nylon, 6,10-nylon, 11-nylon, 12-nylon, as well as resins formed by chemically modifying nylon such as N-alkoxy methyl modified nylon and N-alkoxy ethyl modified nylon.

The intermediate layer 15 may contain particles such as metal oxide particles. By incorporation of the particles in the intermediate layer 15, the volumic resistance value of the intermediate layer 15 can be controlled to enhance the effect of preventing injection of the charges from the conductive substrate 11 to the photosensitive layer 14. Moreover, electric characteristics of the photoreceptor 2 can be maintained under various circumstances to improve the circumstantial stability. The metal oxide particles can include, for example, particles of titanium oxide, aluminum oxide, aluminum hydroxide and tin oxide.

The intermediate layer 15 can be formed, for example, by preparing a coating solution for intermediate layer by dissolving or dispersing the resin described above into an appropriate solvent and coating the coating solution on the surface of the conductive substrate 11. In a case where the particles such as metal oxide particles described above are incorporated in the intermediate layer 15, the intermediate layer 15 can be formed by dispersing the particles in a resin solution obtained by dissolving the resin into an appropriate solvent to prepare a coating solution for intermediate layer and coating the coating solution on the surface of the conductive substrate 11.

As the solvent of the coating solution for intermediate layer, water, various organic solvents or a mixed solvent thereof is used. Among them, a single solvent such as water, methanol, ethanol or butanol; or a mixed solvent such as of water and alcohol, two or more kinds of alcohols, acetone or dioxolane and alcohols, chloro solvent such as dichloroethane, chloroform or trichloroethane and alcohols is used preferably.

As the method of dispersing the particles in the resin solution, a known dispersion method using, for example, a ball mill, sand mill, attritor, vibration mill, supersonic dispersing machine or paint shaker can be used.

The ratio of the total weight (C) of the resin and the metal oxide to the weight (D) of the solvent used in the intermediate layer-forming coating liquid, C/D is preferably from 1/99 to 40/60, more preferably from 2/98 to 30/70. The ratio of the weight (E) of the resin tot he weight (F) of the metal oxide, E/F is preferably from 90/1 to 1/99, more preferably from 70/30 to 5/95.

The coating method for the coating solution for intermediate layer can include, for example, a spraying method, bar coating method, roll coating method, blade method, wringing method and dip coating method. Among them, since the dip coating method is relatively simple and excellent in view of the productivity and the cost as described above, it is used suitably also in a case of forming the intermediate layer 15.

The thickness of the intermediate layer 15 is, preferably, 0.01 μm or more and 20 μm or less and, more preferably, 0.05 μm or more 10 μm or less. In a case where the thickness of the intermediate layer 15 is less than 0.01 μm, it no more functions substantially as the intermediate layer 15, and uniform surface property by covering the defects of the conductive substrate 11 can not be obtained to result in a worry of not capable of preventing injection of charges from the conductive substrate 11 to the photosensitive layer 14 to possibly lower the chargeability of the photosensitive layer 14. Increase of the thickness of the intermediate layer 15 to more than 20 μm is not preferable since the formation of the intermediate layer 15 is difficult in a case of forming the intermediate layer 15 by the dip coating method and the photosensitive layer 14 can not be formed uniformly over the intermediate layer 15 to possibly lower the sensitivity of the photoreceptor 2.

Also in this embodiment, various kinds of additives such as a plasticizer, leveling agent or fine particles of organic compound or inorganic compound may also be added to the charge transporting layer 13 like in the first embodiment. Further, a sensitizers such as an electron accepting substance or dye, an anti-oxidant or additive such as a UV-absorbent may also be added to each of the layers 12 and 13 of the photosensitive layer 14.

FIG. 3 is a fragmentary cross sectional view schematically showing the constitution of an electrophotographic photoreceptor 3 as a third embodiment of the electrophotographic photoreceptor according to the invention. The electrophotographic photoreceptor 3 of this embodiment is similar to the electrophotographic photoreceptor 2 of the second embodiment shown in FIG. 2 in which corresponding portions carry identical reference numerals for which descriptions are to be omitted.

What is to be noted in the electrophotographic photoreceptor 3 is that the photosensitive layer 140 has a single-layered structure comprising a single layer containing both the charge generating substance and the charge transporting substance. That is, the photoreceptor 3 is a single-layered type photoreceptor.

The single-layered photoreceptor 3 of this embodiment is suitable as a photoreceptor for use in a positively charged image forming apparatus with less generation of ozone and, since the photosensitive layer 140 to be coated consists of only one layer, the production cost and the yield are excellent compared with the laminated type photoreceptors 1 and 2 of the first embodiment and the second embodiment.

The photosensitive layer 140 may be formed by binding the hydrazone compound of formula (1) of the invention and optionally any other charge transporting substance, and the charge generating substance as above, with a binder resin. For the binder resin, usable are those mentioned hereinabove for the binder resin in the charge transporting layer 13 of the first embodiment of the invention. Like the photosensitive layer 14 in the first embodiment, the photosensitive layer 140 may also contain various additives added thereto such as plasticizer, leveling agent, fine particles of inorganic compound or organic compound, sensitizer such as electron-accepting substance or dye, antioxidant and UV absorbent.

The photosensitive layer 140 may be formed in the same manner as that for the charge transporting layer 13 to be provided in the photoreceptor 1 of the first embodiment. For example, a suitable amount of the charge generating substance as above, the hydrazone compound of formula (1) of the invention and binder resin, and optionally a suitable amount of any other charge transporting substance than the hydrazone compound of the invention and additives are dissolved or dispersed in a suitable solvent like that for the charge transporting layer-forming coating liquid as above, to thereby prepare a photosensitive layer-forming coating liquid, and the photosensitive layer-forming coating liquid is applied onto the intermediate layer 15 according to a dipping method to thereby form the photosensitive layer 140.

The ratio of the weight (B') of the binder resin to the weight (A') of the hydrazone compound of formula (1) in the photosensitive layer 140, B'/A' is preferably from 1.2 to 3.0, like the ratio, B/A, of the weight (B) of the binder resin to the weight (A) of the hydrazone compound of formula (1) in the charge transporting layer 13 of the first embodiment mentioned above.

The thickness of the photosensitive layer 140 is, preferably, 5 μm or more and 100 μm or less and, more preferably, 10 μm or more and 50 μm or less. In a case where the thickness of the photosensitive layer 140 is less than 5 μm, the charge retainability on the surface of the photoreceptor may possibly be lowered. In a case where the thickness of the photosensitive layer 140 exceeds 100 μm, the productivity may possibly be lowered.

The electrophotographic photoreceptor according to the invention is not restricted to the constitution for the electrophotographic photoreceptors 1, 2, 3 of the first embodiment to the third embodiment shown in FIG. 1 to FIG. 3 described previously but it may be of other different constitutions so long as the hydrazone compound according to the invention represented by the general formula (1) is contained in the photosensitive layer.

For example, it may be of such a constitution that a surface protective layer is provided on the surface of the photosensitive layer 14 or 140. Mechanical durability of the photoreceptor 1, 2 or 3 can be improved by providing surface protective layer on the surface of the photosensitive layer 14 or 140. Further, it can prevent undesired chemical effects of an active gas such as ozone or nitrogen oxide (NOx) generated by corona discharge in charging the surface of the photoreceptor on the photosensitive layer 14 or 140. As a result, electrical durability of the photoreceptor 1, 2 or 3 can be improved. As the surface protective layer, a layer comprising, for example, a resin, an inorganic filler-containing resin or inorganic oxide is used.

Then, the image forming apparatus having the electrophotographic photoreceptor according to the invention is to be described. The image forming apparatus according to the invention is not restricted to the following contents of the description.

FIG. 4 is a side elevational view for the arrangement schematically showing the constitution of an image forming apparatus 100 as an embodiment of the image forming apparatus according to the invention. The image forming apparatus 100 shown in FIG. 4 has, mounted thereon, a photoreceptor 1 shown in FIG. 1 as described above as a first embodiment of the electrophotographic photoreceptor according to the invention. The constitution of the image forming apparatus 100 and the image forming operation thereof are to be described with reference to FIG. 4.

The image forming apparatus 100 has the photoreceptor 1 supported rotationally on an apparatus main body (not shown) and driving means (not shown) for rotationally driving the photoreceptor 1 in the direction of an arrow 41 around a rotational axis 44. The driving means comprises, for example, a motor as a driving source and rotationally drives the photoreceptor 1 at a predetermined circumferential speed Vp (herein after the circumferential speed Vp is also referred to as the rotational circumferential speed Vp of the photoreceptor 1) by transmitting the power from the motor by way of gears (not shown) to a support that constitutes the core of the photoreceptor 1.

At the periphery of the photoreceptor 1, are provided a charger 32, exposure means 30, a developing device 33, a transfer device 34 and a cleaner 36 in this order from the upstream to the downstream in the rotational direction of the photoreceptor 1 shown by an arrow 41. The cleaner 36 is provided together with a charge elimination lamp (not shown).

The charger 32 is charging means for charging the surface 43 of the photoreceptor 1 to a predetermined potential. The charger 32 is, for example, contact type charging means such as a charging roller.

The exposure means 30 has, for example, a semiconductor laser as a light source, exposes the surface 43 of the charged photoreceptor 1 by a light 31 of a laser beam or the like outputted in accordance with the image information from the light source to thereby form static latent images on the surface 43 of the photoreceptor 1.

The developing device 33 is developing means for developing static latent images formed on the surface 43 of the photoreceptor 1 with the developer thereby forming toner image as visible images and it comprises a developing roller 33a opposed to the photoreceptor 1 and supplying a toner to the surface 43 of the photoreceptor 1 and a casing 33b for rotationally supporting the developing roller 33a around the rotational axis parallel with the rotational axis 44 of the photoreceptor 1, and containing a toner-containing developer to the inner space thereof.

The transfer device 34 is transfer means for transferring the toner images formed on the surface 43 of the photoreceptor 1 from the surface 43 of the photoreceptor 1 to recording paper 51 as a transfer material. The transfer device 34 is non-contact type transfer means which has charging means, for example, a corona discharger and which transfers toner images onto the recording paper 51 by applying charges of a polarity opposite to that of the toner to the recording paper 51.

The cleaner 36 is cleaning means for cleaning the surface of the photoreceptor 1 after transfer of the toner images and comprises a cleaning blade 36a pressed to the surface 43 of the photoreceptor for peeling the toner remaining on the surface 43 of the photoreceptor 1 after transfer operation by the transfer device 34 from the surface 43, and a recovery casing 36b for containing the toner peeled by the cleaning blade 36a.

Further, the fixing device 35 as fixing means is provided for fixing the transferred toner images in the direction along which the recording paper 51 is conveyed after passage between the photoreceptor 1 and the transfer device 34. The fixing device 35 comprises a heating roller 35a having heating means (not shown) and a pressing roller 35b opposed to the heating roller 35a for forming an abutting portion being pressed by the heating roller 35a.

The image forming operation by the image forming apparatus 100 is to be described. At first, in accordance with an instruction from a control section (not shown), the photoreceptor 1 is rotationally driven by the driving means along the direction of an arrow 41 and the surface 43 thereof is charged uniformly to a predetermined positive or negative potential by the charger 32 situated upstream of the focussing point of a light 31 from the exposure means 30 in the rotational direction to the photoreceptor 1.

Then, in accordance with the instruction from the control section, the light 31 is irradiated from the exposure means 30 to the charged surface 43 of the photoreceptor 1. The light 31 from the light source is scanned repetitively in the longitudinal direction of the photoreceptor 1 as a main scanning direction based on the image information. By rotationally driving the photoreceptor 1 to scan the light 31 from the light source repetitively based on the image information, exposure corresponding to the image information can be applied to the surface 43 of the photoreceptor 1. By the exposure, the surface charges at a portion irradiated with the light 31 are decreased to cause difference between the surface potential at a portion where the light 31 has been irradiated and the surface potential at a portion where the light 31 has not been irradiated, to form static latent images on the surface 43 of the photoreceptor 1. Further, in synchronization with the exposure to the photoreceptor 1, the recording paper 51 is supplied by the conveying means from the direction of the arrow 42 to the transfer position between the transfer device 34 and the photoreceptor 1.

Then, a toner is supplied from the developing roller 33a of the developing device 33 situated to the downstream of the focusing point of the light 31 from the light source in the rotational direction of the photoreceptor 1 to the surface 43 of the photoreceptor 1 formed with the static latent images. This develops the static latent images to form toner images as visible images to the surface 43 of the photoreceptor 1. When the recording paper 51 is supplied between the photoreceptor 1 and the transfer device 34, charges at a polarity opposite to that of the toner are given by the transfer device 34 to the recording paper 51 thereby transferring the toner images formed on the surface 43 of the photoreceptor 1 to the recording paper 51.

The recording paper 51 transferred with the toner images is conveyed by the conveying means to the fixing device 35 and heated and pressed in passing the abutted portion between the heating roller 35a and the pressing roller 35b of the fixing device 35. This fixes the toner images on the recording paper 51 to form firm images. The recording paper 51 thus formed with the images is discharged by conveying means to the outside of the image forming apparatus 100.

On the other hand, after transfer of the toner images to the recording paper 51, the photoreceptor 1 that rotates further in the direction of the arrow 41 is rubbed at the surface 43 by the cleaning blade 36a provided to the cleaner 36 and cleaned. The surface 43 of the photoreceptor 1 thus removed with the toner is charge-eliminated by the light from the charge illumination lamp, by which the static latent images on the surface 43 of the photoreceptor 1 are eliminated. Then, the photoreceptor 1 is further driven rotationally, and a series of operation starting from charging are repeated again. As described above, images are formed continuously.

The photoreceptor 1 equipped in the image forming apparatus 100 contains, as so mentioned hereinabove, the hydrazone compound of formula (1) of the invention in the photosensitive layer 14 as the charge transporting substance therein, and it has good electric properties such as good chargeability, sensitivity and light responsibility, and has good electric and mechanical durability and good environment stability. Accordingly, the image forming apparatus 100 realizes high reliability ensuring stable formation of high-quality images for a long period of time in various environments. In addition, since the electric properties of the photoreceptor 1 do not worsen even through exposure to external light, the image quality depression owing to the exposure of the photoreceptor 1 to external light during maintenance may be prevented.

Further, since the photoreceptor 1 does not result in lower the picture quality even in a case where it is used for a high speed electrophotographic process, the image forming speed of the image forming apparatus 100 can be increased. Images at high quality can be provided, for example, also by using a photoreceptor of 30 mm diameter and 340 mm length in the longitudinal direction, and conducting an electrophotographic process at high speed while setting the rotational circumferential speed Vp of the photoreceptor 1 to about 100 to 140 mm on every sec and forming images at a image forming speed of the image forming apparatus 100 to a high speed of about 25 sheets of A4 size paper/min specified according to JIS P 0138.

The image forming apparatus according to the invention is not restricted to the constitution of the image forming apparatus 100 shown in FIG. 4 but it may be of any other different constitution so long as the photoreceptor according to the invention can be used therein.

For example, while the charger 32 is the contact type charging means in the image forming apparatus 100 of this embodiment, this is not restrictive thereto but may be no-contact type charging means such as a corona discharger. Further, while the transfer device 34 is the no-contact type transfer means for conducting transfer without using a pressing force, this is not restrictive but may be contact type transfer means of conducting transfer by utilizing the pressing force. As the contact type transfer means, those, for example, having a transfer roller, pressing the transfer roller to the photoreceptor 1 from the side opposite to the abutting surface of the recording paper 51 that is abutted against the surface 43 of the photoreceptor 1, and applying a voltage to the transfer roller in a state where the photoreceptor 1 and the recording paper 51 are in press contact with each other thereby transferring the toner images onto the recording paper 51 can be used.

EXAMPLE

The present invention is to be described further specifically with reference to preparation examples, examples and comparative examples but the invention is not restricted to the following descriptions.

Production Examples

Production Example 1

Production of Compound No. 1

Acetophenone was used as the ketone compound of formula (4a), and N,N-diphenylhydrazine was used as the hydrazine compound of formula (4b), and these were reacted in a mode of dehydrating condensation mentioned below to produce a hydrazone intermediate having the following structural formula (8):

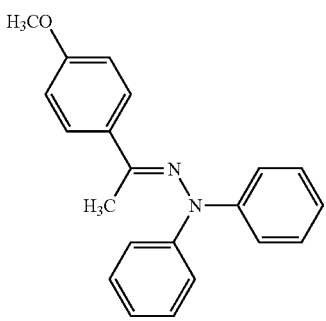

(8)

15.1 g (1.0 mol equivalent) of p-methoxyacetophenone, 19.5 g (1.05 mol equivalent) of N,N-diphenylhydrazine, and, as a catalyst, 0.06 ml (0.01 mol equivalents) of acetic acid were added to 100 ml of ethanol, and reacted for 4 hours with stirring under heat at 80° C. The reaction solution was left cooled, and 100 ml of hexane was added to it, and the precipitated crystal was taken out through filtration. This was dried under reduced pressure to obtain 27.8 g of a hydrazone intermediate of formula (8) as an yellow crystal (yield, 88.0%).

Next, acetyl chloride was used as the acyl halide compound of formula (7a), and the hydrazone intermediate of formula (8) was acylated in the manner mentioned below to produce a hydrazone-ketone intermediate having the following structural formula (9):

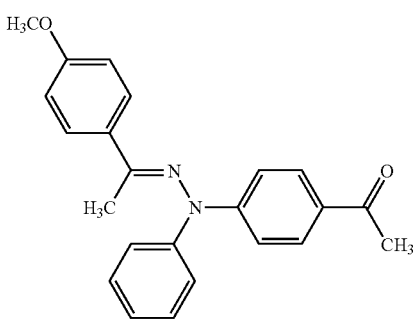

(9)

With cooling with ice, 5.55 g (1.4 mol equivalents) of acetyl chloride was gradually added to 100 ml of anhydrous methylene chloride with 8.0 g (1.2 mol equivalents) of aluminium chloride suspended therein, and stirred for about 30 minutes to prepare a Friedel-Craft acetylation reagent. To this solution, gradually added was 15.82 g (1.0 mol equivalent) of the hydrazone intermediate of formula (8) with cooling with ice. Next, this was gradually heated up to its reaction temperature of 30° C., and while heated so as to keep it at 30° C., this was reacted with stirring for 3 hours. After the reaction, the reaction solution was left cooled, and this was gradually added to 400 ml of a cooled, aqueous 4 N sodium hydroxide solution to form a precipitate therein. The resulting precipitate was taken out through filtration, well washed with water, and recrystallized from a mixed solvent of ethanol and ethyl acetate to obtain 16.12 g of an yellow powdery compound.

Analyzing the compound through liquid chromatography-mass spectrometry (LC-MS) gave a peak at 359.4 corresponding to the molecular ion $[M+H]^+$ of the intended compound, hydrazone-ketone intermediate of formula (9) (calculated molecular weight: 358.18) with a proton added thereto. This confirms that the compound obtained herein is the hydrazone-ketone intermediate of formula (9) (yield, 90.0%) The LC-MS analysis of the compound further confirmed that the purity of the hydrazone-ketone intermediate obtained herein is 98.1%.

Next, 1.94 g (1.2 mol equivalents) of cinnamyl bromide having the following structural formula (10), as the allyl halide compound of formula (6b) mentioned above, and 240 mg (1.2 mol equivalents) of a metal magnesium powder were added to 20 ml of anhydrous THF and stirred to prepare a Grignard reagent.

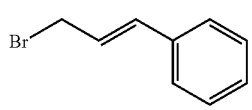

(10)

With cooling with ice, 2.94 g (1.0 mol equivalent) of the hydrazone-ketone intermediate of formula (9) produced in the manner as above was gradually added to the Grignard reagent solution. Next, the reaction solution was stirred at room temperature for 1 hour, then heated up to 40° C., and still kept heated at 40° C., this was reacted with stirring for 5 hours. The reaction solution was left cooled, and then poured into excess methanol. The resulting precipitate was taken out through filtration, and dissolved in toluene to prepare a toluene solution. The toluene solution was transferred into a liquid-liquid separation funnel and washed with water, and then the organic layer was taken out. Thus taken out, the organic layer was dried with magnesium sulfate. After dried, the solid deposit was removed and the resulting organic layer was concentrated and subjected to silica gel column chromatography to obtain 3.20 g of an yellow crystal.

Analyzing the compound through LC-MS gave a peak at 459.3 corresponding to the molecular ion $[M+H]^+$ of the intended hydrazone-diene compound, Compound No. 1 in Table 1 (calculated molecular weight: 458.24) with a proton added thereto. This confirms that the crystal obtained herein is the hydrazone-diene compound, Compound No. 1 (yield, 85%).

The LC-MS analysis of the compound further confirmed that the purity of the hydrazone compound, Compound No. 1 obtained herein is 99.5%. Elementary analysis of Compound No. 1 obtained herein gave the data mentioned below. The elementary analysis of Compound No. 1 was carried out in a mode of differential thermal conductivity analysis for simultaneous quantification of carbon (C), hydrogen (H) and nitrogen (N). The same shall apply to the other Production Examples given hereinunder.

<Elementary Analysis Data of Compound No. 1>

| Theoretical: | C 83.81%, H 6.59%, N 6.11% |
|---|---|
| Found: | C 83.67%, H 6.44%, N 6.01% |

Production Example 2

Production of Compound No. 18

3.30 g of an yellow powdery compound was obtained in the same manner as in Production Example 1, for which, however, 2.2 g (1.2 mol equivalents) of 5-bromo-1-phenyl-1,3-pentadiene having the following structural formula (11) was used in place of cinnamyl bromide (1.2 mol equivalents) of formula (10) in the Grignard reaction in Production Example 1.

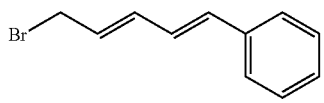
(11)

Analyzing the compound through LC-MS gave a peak at 485.4 corresponding to the molecular ion [M+H]$^+$ of the intended hydrazone-hexatriene compound, Compound No. 18 in Table 1 (calculated molecular weight: 484.25) with a proton added thereto. This confirms that the compound obtained herein is the hydrazone-hexatriene compound, Compound No. 18 (yield, 81.0%).

The LC-MS analysis of the compound further confirmed that the purity of the hydrazone compound, Compound No. 18 obtained herein is 98.9%. Elementary analysis of Compound No. 18 obtained herein gave the following data.

<Elementary Analysis Data of Compound No. 18>

| Theoretical: | C 84.67%, H 6.71%, N 5.49% |
|---|---|
| Found: | C 84.51%, H 6.58%, N 5.38% |

Production Example 3

Production of Compound No. 28

A hydrazone intermediate having the following structural formula (12) was obtained as an yellow crystal in the same manner as in Production Example 1, for which, however, 3,4-methylenedioxybenzaldehyde was used in place of p-methoxyacetophenone (yield, 98%).

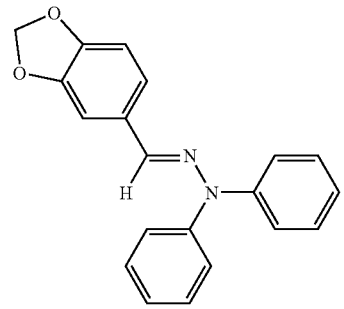
(12)

Next, with cooling with ice, 9.2 g (1.2 mol equivalents) of phosphorus oxychloride was gradually added to 100 ml of anhydrous N,N-dimethylformamide (DMF), and stirred for about 30 minutes to prepare a Vilsmeier reagent. With cooling with ice, 15.82 g (1.0 mol equivalent) of the hydrazone intermediate of formula (12) obtained in the manner as above was gradually added to the Vilsmeier reagent solution. Next, this was gradually heated up to its reaction temperature of 70° C., and while heated so as to keep it at 70 to 80° C., this was reacted with stirring for 3 hours. After the reaction, the reaction solution was left cooled, and this was gradually added to 800 ml of a cooled, aqueous 4 N sodium hydroxide solution to form a precipitate therein. The resulting precipitate was taken out through filtration, well washed with water, and recrystallized from a mixed solvent of ethanol and ethyl acetate to obtain 14.6 g of an yellow powdery compound.

Analyzing the compound through LC-MS gave a peak at 345.8 corresponding to the molecular ion [M+H]$^+$ of the intended hydrazone-aldehyde intermediate having the following structural formula (13) (calculated molecular weight: 344.31) with a proton added thereto. This confirms that the compound obtained herein is the hydrazone-aldehyde intermediate of formula (13) (yield, 85%). The LC-MS analysis of the compound further confirmed that the purity of the hydrazone-aldehyde intermediate obtained herein is 99.0%.

(13)

Next, 7.00 g (1.0 mol equivalent) of the hydrazone-aldehyde intermediate of formula (13) obtained herein, and 6.1 g (1.2 mol equivalents) of diethylcinnamyl phosphonate having the following structural formula (14), as the Wittig reagent of formula (6) mentioned above, were added to 80 ml of anhydrous DMF and dissolved, and then, with cooling to 0° C., 2.8 g (1.25 mol equivalents) of potassium t-butoxide was gradually added to the solution.

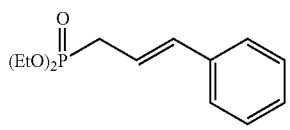

(wherein Et represents an ethyl group).

Next, the reaction solution was stirred at room temperature for 1 hour, and then heated up to 40° C., and, while still kept heated at 40° C., this was further reacted with stirring for 5 hours. The reaction solution was left cooled, and then poured into excess methanol. The resulting precipitate was taken out through filtration, and dissolved in toluene to be a toluene solution. The toluene solution was transferred into a liquid-liquid separation funnel and washed with water, and the organic layer was taken out. Thus taken out, the organic layer was dried with magnesium sulfate. After dried, the solid deposit was removed, and the organic layer was concentrated and subjected to silica gel column chromatography to obtain 8.0 g of an yellow crystal.

Analyzing the crystal through LC-MS gave a peak at 445.6 corresponding to the molecular ion [M+H]$^+$ of the intended hydrazone compound, Compound No. 28 in Table 3 (calculated molecular weight: 444.18) with a proton added thereto. This confirms that the crystal obtained herein is the hydrazone compound, Compound No. 28 (yield, 89%).

The LC-MS analysis of the compound further confirmed that the purity of Compound No. 28 obtained herein is 99.1%. Elementary analysis of Compound No. 28 gave the data mentioned below.

<Elementary Analysis Data of Compound No. 28>

| Theoretical: | C 81.06%, H 5.44%, N 6.30% |
| --- | --- |
| Found: | C 79.97%, H 5.31%, N 6.18% |

Production Example 4

Production of Compound No. 55

A hydrazone-aldehyde intermediate having the following structural formula (15) was produced in the same manner as in Production Example 3, for which, however, 3,4-methylenedioxyacetophenone was used in place of 3,4-methylenedioxybenzaldehyde.

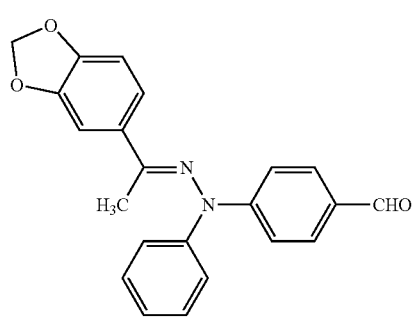

Next, 1.57 g (1.0 mol equivalent) of the hydrazone-aldehyde intermediate of formula (15) obtained herein, and 1.53 g (1.2 mol equivalents) of a Wittig reagent having the following structural formula (16) were added to 15 ml of anhydrous DMF and dissolved, and then, with cooling to 0° C., 0.64 g (1.25 mol equivalents) of potassium t-butoxide was gradually added to the solution.

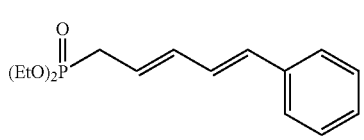

(wherein Et represents an ethyl group).

Next, the reaction solution was stirred at room temperature for 1 hour, and then heated up to 40° C., and, while still kept heated at 40° C., this was further reacted with stirring for 5 hours. The reaction solution was left cooled, and then poured into excess methanol. The resulting precipitate was taken out through filtration, and dissolved in toluene to be a toluene solution. The toluene solution was transferred into a liquid-liquid separation funnel and washed with water, and the organic layer was taken out. Thus taken out, the organic layer was dried with magnesium sulfate. After dried, the solid deposit was removed, and the organic layer was concentrated and subjected to silica gel column chromatography to obtain 1.67 g of an yellow crystal.

Analyzing the crystal through LC-MS gave a peak at 471.7 corresponding to the molecular ion [M+H]$^+$ of the intended hydrazone compound, Compound No. 55 in Table 4 (calculated molecular weight: 470.20) with a proton added thereto. This confirms that the crystal obtained herein is the hydrazone compound, Compound No. 55 (yield, 78%).

The LC-MS analysis of the compound further confirmed that the purity of Compound No. 55 obtained herein is 99.7%. Elementary analysis of Compound No. 55 gave the data mentioned below.

<Elementary Analysis Data of Compound No. 55>

| Theoretical: | C 82.33%, H 5.92%, N 6.27% |
| --- | --- |
| Found: | C 82.17%, H 5.78%, N 6.15% |

Production Example 5

Production of Compound No. 45

Compound No. 45 was produced in the same manner as in Production Example 1, for which, however, the starting compounds shown in Table 5 below were used as the ketone compound of formula (4a), the hydrazine compound of formula (4b), the acyl halide compound of formula (7a) and the allyl halide compound of formula (6b). In addition to these, Table 5 shows the starting compounds for Compounds No. 1 and No. 18.

TABLE 5

| Compound No. | Formula (4a) | Formula (4b) | Formula (7a) | Formula (6b) |
|---|---|---|---|---|
| No. 1 (Production Example 1) | H₃CO–C₆H₄–C(=O)CH₃ | H₂N–N(C₆H₅)₂ | CH₃C(=O)Cl | Br–CH₂–CH=CH–C₆H₅ |
| No. 18 (Production Example 2) | H₃CO–C₆H₄–C(=O)CH₃ | H₂N–N(C₆H₅)₂ | CH₃C(=O)Cl | Br–CH₂–CH=CH–CH=CH–C₆H₅ |
| No. 45 (Production Example 5) | α-tetralone | H₂N–N(benzyl)(3-ethylphenyl) | 2,6-dimethylphenyl (CH₃ groups shown) | 4-(phenylthio)phenyl |

Production Examples 6 to 14

Compounds Nos. 6, 8, 9, 14, 30, 32, 43, 53 and 59 were produced in the same manner as in Production Example 3, for which, however, the starting compounds shown in Tables 6 and 7 below were used as the ketone compound of formula (4a), the hydrazine compound of formula (4b) and the Wittig reagent of formula (6). In addition to these, Tables 6 and 7 show the starting compounds for Compounds No. 28 and No. 55. In Tables 6 and 7, Et represents an ethyl group.

TABLE 6

| Compound No. | Formula (4a) | Formula (4b) | Formula (6) |
|---|---|---|---|
| No. 6 (Production Example 6) | H₃CO–C₆H₄–CHO | H₂N–N(CH₃)(C₆H₅) | (EtO)₂P(=O)–CH₂–CH=CH–C₆H₄–CH₃ |
| No. 8 (Production Example 7) | H₃CO–C₆H₄–CHO | H₂N–N(benzyl)(C₆H₅) | (EtO)₂P(=O)–CH₂–CH=CH–C₆H₄–CH₃ |

TABLE 6-continued

| Compound No. | Formula (4a) | Formula (4b) | Formula (6) |
|---|---|---|---|
| No. 9 (Production Example 8) | 4-methoxybenzaldehyde | N-benzyl-N-(4-methoxyphenyl)phenylhydrazine | (EtO)$_2$P(O)CH$_2$CH=C(CH$_3$)-C$_6$H$_4$-CH$_2$CH$_2$F |
| No. 14 (Production Example 9) | 4-methoxybenzaldehyde | 1,1-diphenylhydrazine | (EtO)$_2$P(O)CH$_2$CH=CH-C$_6$H$_4$-OCH$_3$ |
| No. 28 (Production Example 2) | piperonal (benzo[1,3]dioxole-5-carbaldehyde) | 1,1-diphenylhydrazine | (EtO)$_2$P(O)CH$_2$CH=CH-C$_6$H$_5$ |
| No. 30 (Production Example 10) | 4-methoxybenzaldehyde | 1-(3-ethylphenyl)-1-(4-methylphenyl)hydrazine | (EtO)$_2$P(O)CH$_2$CH=CH-CH=C(4-MeO-C$_6$H$_4$)$_2$ |
| No. 32 (Production Example 11) | furan-2-carbaldehyde | 1-(3-n-propylphenyl)-1-(4-methylphenyl)hydrazine | (EtO)$_2$P(O)CH$_2$CH=C(C$_6$H$_5$)CH$_2$C$_6$H$_5$ |

TABLE 7

| Compound No. | Formula (4a) | Formula (4b) | Formula (6) |
|---|---|---|---|
| No. 43 (Production Example 12) | 4-methoxyphenyl 2-furyl ketone (H₃CO-C₆H₄-C(=O)-furan) | 1-benzyl-1-(3-methylphenyl)hydrazine (H₂N-N(CH₂Ph)(3-CH₃-C₆H₄)) | (EtO)₂P(=O)-CH₂-C(=CH-Ph)-CH₂-Ph |
| No. 53 (Production Example 13) | 4'-methylacetophenone (4-CH₃-C₆H₄-C(=O)-CH₃) | 1-(2-methylphenyl)-1-(4-phenylthiophenyl)hydrazine (H₂N-N(2-CH₃-C₆H₄)(4-PhS-C₆H₄)) | (EtO)₂P(=O)-CH(CH₃)-C(CH₃)=CH-CH=CH-Ph |
| No. 55 (Production Example 4) | 3,4-methylenedioxyacetophenone | 1,1-diphenylhydrazine (H₂N-N(Ph)₂) | (EtO)₂P(=O)-CH₂-CH=CH-CH=CH-Ph |
| No. 59 (Production Example 14) | 4-methylbenzaldehyde (4-CH₃-C₆H₄-CHO) | 1-(2-fluorophenyl)-1-(3-ethylphenyl)hydrazine (H₂N-N(2-F-C₆H₄)(3-C₂H₅-C₆H₄)) | (EtO)₂P(=O)-CH(CH₃)-C(CH₃)=CH-CH=CH-Ph |

Elementary analysis data of the compounds obtained in Production Examples 1 to 14 are shown in Table 8 below.

TABLE 8

| Compound No. | Theoretical C (%) | Theoretical H (%) | Theoretical N (%) | Found C (%) | Found H (%) | Found N (%) |
|---|---|---|---|---|---|---|
| No. 1 | 83.81 | 6.59 | 6.11 | 83.67 | 6.44 | 6.01 |
| No. 6 | 81.58 | 7.35 | 7.05 | 81.43 | 7.20 | 6.97 |
| No. 8 | 83.81 | 6.59 | 6.11 | 83.75 | 6.50 | 5.97 |
| No. 9 | 78.62 | 6.60 | 5.24 | 78.51 | 6.49 | 5.14 |
| No. 14 | 80.84 | 6.13 | 6.08 | 80.69 | 6.01 | 5.97 |
| No. 18 | 84.67 | 6.71 | 5.49 | 84.51 | 6.58 | 5.38 |
| No. 28 | 81.06 | 5.44 | 6.30 | 79.97 | 5.31 | 6.18 |
| No. 30 | 83.12 | 6.56 | 3.80 | 83.01 | 6.47 | 3.68 |
| No. 32 | 85.04 | 6.76 | 5.22 | 84.91 | 6.68 | 5.09 |
| No. 43 | 84.01 | 6.23 | 4.56 | 83.97 | 6.09 | 4.49 |
| No. 45 | 88.01 | 7.21 | 4.77 | 87.89 | 7.04 | 4.59 |
| No. 53 | 81.78 | 6.71 | 4.24 | 81.59 | 6.57 | 4.11 |
| No. 55 | 82.33 | 5.92 | 6.27 | 82.17 | 5.78 | 6.15 |
| No. 59 | 84.41 | 6.90 | 5.18 | 84.28 | 6.75 | 5.04 |

EXAMPLE

Example 1

After adding 1 part by weight of an azo compound represented by the following structural formula (17) as a charge generating substance to a resin solution obtained by dissolving 1 part by weight of a phenoxy resin (PKHH: manufactured by Union Carbide Co.) to 99 parts by weight of tetrahydrofuran (THF), they were dispersed for 2 hours by a paint shaker to prepare a coating solution for use in charge generating layer. After coating the coating solution for use in charge generating layer on aluminum for a conductive substrate prepared by vapor depositing aluminum on the surface of a polyester film of 80 μm thickness by a Baker applicator, it was dried to form a charge generating layer of 0.3 μm thickness.

Then, 8 parts by weight of the hydrazone compound of Exemplified Compound No. 1 shown in Table 1 as a charge transporting substance and 10 parts by weight of a polycarbonate resin (C-1400: manufactured by Teijin Kasei Co.) were dissolved in 80 parts by weight of THF to prepare a coating solution for use in charge transporting layer. After coating the coating solution for use in charge transporting layer to the charge generating layer formed previously by a Baker applicator, it was dried to form a charge transporting layer of 10 μm thickness.

As described above, an electrophotographic photoreceptor of Example 1 having a laminated type layer structure shown in FIG. 1 was manufactured.

Examples 2 to 4

Electrophotographic photoreceptors of Examples 2 to 4 were manufactured in the same manner as in Example 1 except for using the amine compound of Exemplified Compound No. 8, 30 or 59 shown in Table 1 to Table 4 instead of the amine compound of Exemplified Compound No. 1 as the charge transporting substance.

Comparative Example 1

Electrophotographic photoreceptor of Comparative Example 1 were manufactured in the same manner as in Example 1 except for using Comparative Compound A represented by the following structural formula (18) instead of Exemplified Compound No. 1 as the charge transporting substance.

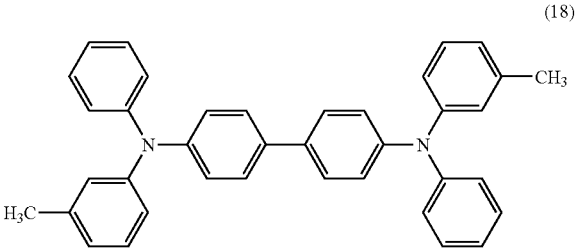

(18)

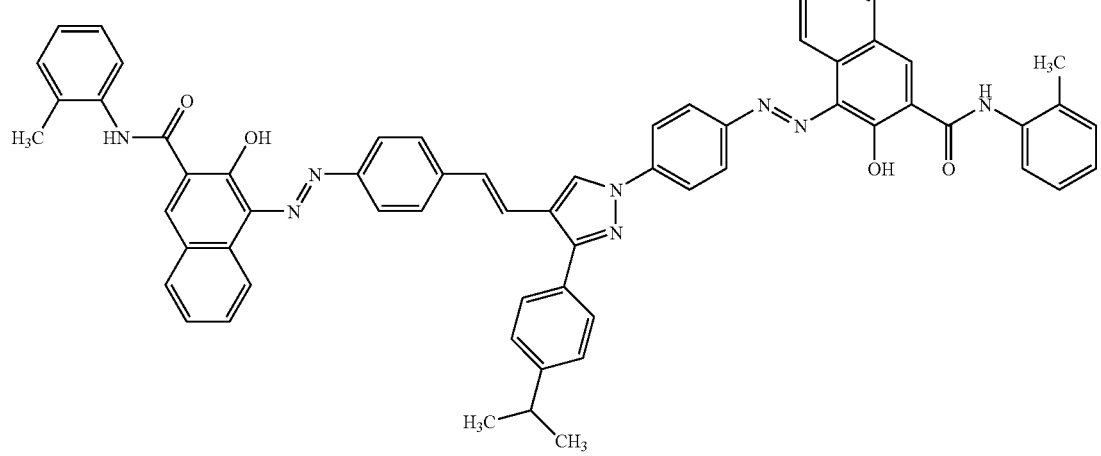

(17)

Comparative Example 2

An electrophotographic photoreceptor of Comparative Example 2 was manufactured in the same manner as in Example 1 except for using a Comparative Compound B represented by the following structural formula (19) instead of Exemplified Compound No. 1 as the charge transporting substance.

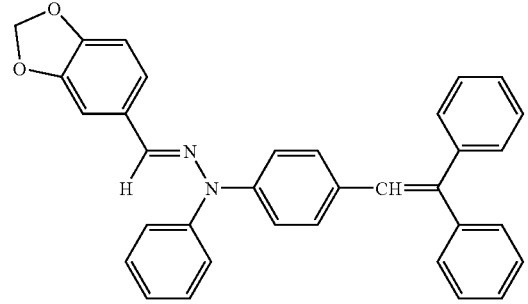

(19)

[Evaluation 1]

The charge mobility of the charge transporting substance used in the photoreceptors produced in Examples 1 to 4 and Comparative Examples 1 and 2 in the manner as above was determined according to the process mentioned below. Concretely, gold was deposited on the surface of the charge transporting layer of each photoreceptor in a mode of vapor deposition, and, while the ambient pressure was reduced under room temperature, the charge mobility (cm$^2$/V·sec) of each sample was determined according to a time-of-flight method. The value is the charge mobility of the charge transporting substance of each photoreceptor. The data are shown in Table 9. In Table 9, the value of the charge mobility is at an electric field intensity of $2.5 \times 10^5$ V/cm.

TABLE 9

| | Charge Transporting Substance | Charge Mobility (cm$^2$/V · sec) |
|---|---|---|
| Example 1 | Compound No. 1 | $5.4 \times 10^{-4}$ |
| Example 2 | Compound No. 8 | $7.4 \times 10^{-4}$ |

After coating the prepared coating solution for use in intermediate layer on a plate-like conductive substrate formed of aluminum of 0.2 mm thickness by a Baker applicator, it was dried to form an intermediate layer of 1 µm thickness.

Then, after adding 2 parts by weight of an azo compound represented by the following structural formula (20) as the charge generating substance to a resin solution obtained by dissolving 1 part by weight of a polyvinyl butyral resin (BX-1: manufactured by Sekisui Chemical Industry Co.) to 97 parts by weight of THF, it was dispersed for 10 hours by a paint shaker to prepare a coating solution for use in charge generating layer. After coating the coating solution for use in charge generating layer on the previously formed intermediate layer by a Baker applicator, it was dried to form a charge generating layer of 0.3 µm thickness.

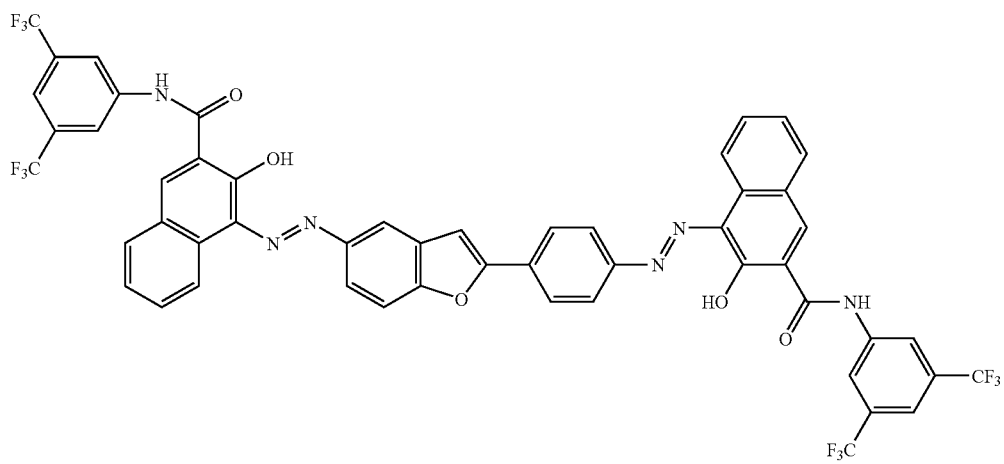

(20)

TABLE 9-continued

| | Charge Transporting Substance | Charge Mobility (cm$^2$/V · sec) |
|---|---|---|
| Example 3 | Compound No. 30 | $6.3 \times 10^{-4}$ |
| Example 4 | Compound No. 59 | $8.1 \times 10^{-4}$ |
| Comparative Example 1 | Comparative Compound A | $1.2 \times 10^{-6}$ |
| Comparative Example 2 | Comparative Compound B | $7.5 \times 10^{-6}$ |

Comparing Examples 1 to 4 with Comparative Examples 1 and 2 confirms that the charge mobility of the hydrazone compounds of formula (1) of the invention is higher by 100 times or more than the comparative compound B, a type of a compound having both a hydrazone stricture and a stilbene structure and corresponding to formula (1) where n=0, and than the comparative compound A triphenyl amine dimer (TPD), a type of a conventionally known charge transporting substance.

Example 5

9 parts by weight of dendritic titanium oxide surface treated with aluminum oxide (chemical formula: $Al_2O_3$) and zirconium dioxide (chemical formula: $ZrO_2$) (TTO-D-1: manufactured by Ishihara Industry Co.) and 9 parts by weight of a copolymerized nylon resin (CM 8000: manufactured by Toray Co.) were added to a solvent mixture comprising 41 parts by weight of 1,3-dioxolan and 41 parts by weight of methanol, and dispersed for 12 hours by using a paint shaker to prepare a coating solution for use in intermediate layer.

Then, 10 parts by weight of the hydrazone compound of Exemplified Compound No. 1 shown in Table 1 as a charge transporting substance, 14 parts by weight of a polycarbonate resin as a binder resin (Z200: manufactured by Mitsubishi Gas Chemical Co.), and 0.2 parts by weight of 2,6-di-t-butyl-4-methylphenol were dissolved in 80 parts by weight of THF, to prepare a coating solution for use in charge transporting layer. After coating the coating solution for use in charge transporting layer on the previously formed charge generating layer by an Baker applicator, it was dried to form a charge transporting layer of 18 µm thickness.

As described above, an electrophotographic photoreceptor of Example 5 having the laminated type layer structure shown in FIG. 2 was manufactured.

Examples 6 to 8

Electrophotographic photoreceptors of Examples 6 to 8 were manufactured in the same manner as in Example 5 except for using Exemplified Compound No. 9, 14 or 32 shown in Table 1 and Table 2 instead of Exemplified Compound No. 1 as a charge transporting substance.

Comparative Examples 3, 4

Electrophotographic photoreceptors of Comparative Examples 3 and 4 were manufactured in the same manner as in Example 5 except for using Comparative Compound A represented by the structural formula (18) mentioned above or Comparative Compound B represented by the structural formula (19) instead of Exemplified Compound No. 1 as a charge transporting substance.

Example 9

In the same manner as in Example 6, an intermediate layer of 1 μm thickness was formed on a plate-like conductive substrate formed of aluminum of 0.2 mm thickness was formed.

Then, 1 part by weight of the azo compound represented by the structural formula (20) as a charge generating substance, 12 parts by weight of a polycarbonate resin (Z-400: manufactured by Mitsubishi Gas Chemical Co.) as a binder resin, 10 parts by weight of the hydrazone compound of Exemplified Compound No. 1 shown in Table 1 as a charge transporting substance, 5 parts by weight of 3,5-dimethyl-3',5'-di-t-butyldiphenoquinone, 0.5 parts by weight of 2,6-di-t-butyl-4-methylphenol and 65 parts by weight of THF were dispersed for 12 hours by a ball mill to prepare a coating solution for use in photosensitive layer. After coating the coating solution for use in photosensitive layer on the previously formed intermediate by a Baker applicator, it was dried at a temperature of 110° C. for one hour by hot blow to form a photosensitive layer of 20 μm thickness.

As described above, an electrophotographic photoreceptor of Example 9 having the single type layer structure shown in FIG. 3 was manufactured.

Example 10

An electrophotographic photoreceptor of Example 10 was manufactured in the same manner as in Example 5 except for using X-type non-metal phthalocyanine instead of the azo compound represented by the structural formula (20) as the charge generating substance.

Examples 11 to 13

Electrophotographic photoreceptor of Examples 11 to 13 were manufactured in the same manner as in Example 5 except for using an X-type non-metal phthalocyanine instead of the azo compound represented by the structural formula (20) as a charge generating substance and using Exemplified Compound No. 6, 45 or 55 shown in Table 1 to Table 4 instead of Exemplified Compound No. 1 as a charge transporting substance.

Comparative Examples 5, 6

Electrophotographic photoreceptors of Comparative Examples 5 and 6 were manufactured in the same manner as in Example 5 except for using an X-type non-metal phthalocyanine instead of the azo compound represented by the structural formula (20) as a charge generating substance and using Comparative Compound A represented by the structural formula (18) or Comparative Compound B represented by the structural formula (19) instead of Exemplified Compound No. 1 as the a transportation material.

[Evaluation 2]

For each of the photoreceptors of Examples 5 to 13 and Comparative Examples 3 to 6 manufactured as described above, initial characteristics and repetitive characteristics were evaluated by using an electrostatic copy paper testing apparatus (EPA-8200: manufactured by Kawaguchi Denki Manufacturing Co.) Evaluation was conducted under each of circumstances, that is, under a normal temperature/normal humidity (N/N) circumstance at a temperature of 22° C. and at a relative humidity of 65% (65% RH) and under a low temperature/low humidity (L/L) circumstance at a temperature of 5° C. and at a relative humidity of 20% (20% RH), respectively.

The initial characteristics were evaluated as described below. The surface of a photoreceptor was charged by applying a voltage at minus (−) 5 kV. The surface potential of the photoreceptor was measured as a charged potential $V_0$ (V) and evaluated such that the chargeability was more excellent as the absolute value of the charged potential $V_0$ was higher. However, in a case of a single layered type photoreceptor of Example 9, the surface of the photoreceptor was charged by applying a voltage at plus (+) 5 kV.

Then, exposure was applied to the charged surface of the photoreceptor. The exposure energy required for decreasing the surface potential of the photoreceptor from the charged potential $V_0$ to one-half level was measured as one-half decay exposure amount $E_{1/2}$ (μJ/cm$^2$) and it was evaluated such that the sensitivity was more excellent as the half-decay exposure amount $E_{1/2}$ was smaller. Further, the surface potential of the photoreceptor at the lapse of 10 sec from the start of the exposure was measured as the residual potential $V_r$ (V) and it was evaluated such that the light responsiveness was more excellent as the absolute value of the residual potential $V_r$ was smaller.

In the exposure, a white light at an exposure energy of 1 μW/cm$^2$ was used in a case of photoreceptors of Examples 5 to 9 and Comparative Examples 3, 4 using the azo compound represented by the structural formula (20) as a charge generating substance, and a coherent light at a wavelength of 780 nm and at an exposure energy of 1 μW/cm$^2$ obtained by spectrolyzation using a monochrometer was used in a case of photoreceptors of Examples 10 to 13 and Comparative Examples 5, 6 using the X-type non-metal phthalocyanine as a charge generating substance.

The repetitive characteristics were evaluated as described below. After repeating the procedure of the charge and the exposure described above as one cycle for 5000 times, the charged potential $V_0$, the one-half decay exposure amount $E_{1/2}$ and the residual potential $V_r$ were measured in the same manner as in the evaluation for the initial characteristics, and the chargeability, the sensitivity and the light responsiveness were evaluated.

The results of measurement described above are shown in Table 10.

TABLE 10

| | | | N/N; 22° C./65% RH | | | | | | L/L; 5° C./20% RH | | | | | |
| | | | Initials Properties | | | Properties after cycle use | | | Initial Properties | | | Properties after cycle use | | |
| | Charge Generating Substance | Charge Transporting Substance | $E_{1/2}$ (μJ/cm$^2$) | V0 (V) | Vr (V) | $E_{1/2}$ (μJ/cm$^2$) | V0 (V) | Vr (V) | $E_{1/2}$ (μJ/cm$^2$) | V0 (V) | Vr (V) | $E_{1/2}$ (μJ/cm$^2$) | V0 (V) | Vr (V) |
|---|---|---|---|---|---|---|---|---|---|---|---|---|---|---|
| Ex. 5 | Azo Compound (20) | Compound No. 1 | 0.19 | −578 | −21 | 0.20 | −580 | −39 | 0.21 | −580 | −30 | 0.23 | −572 | −45 |
| Ex. 6 | Azo Compound (20) | Compound No. 9 | 0.18 | −581 | −20 | 0.20 | −584 | −40 | 0.20 | −583 | −31 | 0.22 | −571 | −47 |
| Ex. 7 | Azo Compound (20) | Compound No. 14 | 0.17 | −574 | −23 | 0.19 | −584 | −41 | 0.21 | −576 | −32 | 0.24 | −564 | −49 |

TABLE 10-continued

|  |  |  | N/N; 22° C./65% RH | | | | | | L/L; 5° C./20% RH | | | | | |
| --- | --- | --- | --- | --- | --- | --- | --- | --- | --- | --- | --- | --- | --- | --- |
|  |  |  | Initials Properties | | | Properties after cycle use | | | Initial Properties | | | Properties after cycle use | | |
|  | Charge Generating Substance | Charge Transporting Substance | $E_{1/2}$ ($\mu J/cm^2$) | V0 (V) | Vr (V) | $E_{1/2}$ ($\mu J/cm^2$) | V0 (V) | Vr (V) | $E_{1/2}$ ($\mu J/cm^2$) | V0 (V) | Vr (V) | $E_{1/2}$ ($\mu J/cm^2$) | V0 (V) | Vr (V) |
| Ex. 8 | Azo Compound (20) | Compound No. 32 | 0.18 | −576 | −25 | 0.21 | −567 | −45 | 0.22 | −579 | −38 | 0.25 | −569 | −52 |
| Comp. Ex. 3 | Azo Compound (20) | Comparative Compound A | 0.23 | −579 | −33 | 0.28 | −565 | −45 | 0.27 | −582 | −50 | 0.30 | −572 | −54 |
| Comp. Ex. 4 | Azo Compound (20) | Comparative Compound B | 0.27 | −580 | −37 | 0.31 | −568 | −70 | 0.32 | −583 | −45 | 0.34 | −571 | −80 |
| Ex. 9 | Azo Compound (20) | Compound No. 1 | 0.26 | 550 | 18 | 0.28 | 540 | 45 | 0.28 | 553 | 33 | 0.32 | 542 | 50 |
| Ex. 10 | X-type Metal-free Phthalocyanine | Compound No. 1 | 0.15 | −581 | −18 | 0.17 | −560 | −28 | 0.13 | −584 | −31 | 0.21 | −574 | −38 |
| Ex. 11 | X-type Metal-free Phthalocyanine | Compound No. 6 | 0.16 | −584 | −19 | 0.18 | −571 | −30 | 0.18 | −587 | −36 | 0.21 | −577 | −45 |
| Ex12. | X-type Metal-free Phthalocyanine | Compound No. 45 | 0.14 | −578 | −21 | 0.17 | −537 | −38 | 0.15 | −582 | −39 | 0.19 | −564 | −47 |
| EX. 13 | X-type Metal-free Phthalocyanine | Compound No. 55 | 0.15 | −581 | −20 | 0.19 | −574 | −39 | 0.16 | −583 | −40 | 0.22 | −569 | −49 |
| Comp. Ex. 5 | X-type Metal-free Phthalocyanine | Comparative Compound A | 0.16 | −583 | −27 | 0.19 | −573 | −41 | 0.18 | −587 | −45 | 0.24 | −571 | −54 |
| Comp. Ex. 6 | X-type Metal-free Phthalocyanine | Comparative Compound B | 0.18 | −576 | −35 | 0.21 | −561 | −45 | 0.20 | −579 | −45 | 0.25 | −532 | −60 |

Table 10 confirms that the photoreceptors of Examples 5 to 13 where the hydrazone compound of formula (1) of the invention was used as the charge transporting substance have good chargeability, sensitivity and light responsibility both under the N/N condition and under the L/L condition. In addition, it further confirms that the photoreceptors of Examples 5 to 13 keep their initial good electric properties even after cycle use.

Example 14

9 parts by weight of dendritic titanium oxide surface treated with aluminum oxide (chemical formula: $Al_2O_3$) and zirconium dioxide (chemical formula: $ZrO_2$) (TTO-D-1: manufactured by Ishihara Industry Co.) and 9 parts by weight of a copolymerized nylon resin (CM 8000: manufactured by Toray Co.) were added to a solvent mixture comprising 41 parts by weight of 1,3-dioxolan and 41 parts by weight of methanol, and dispersed for 8 hours by using a paint shaker to prepare a coating solution for use in intermediate layer. The coating solution for use in intermediate layer was filled in a coating tank, and a cylindrical conductive substrate formed of aluminum having 40 mm diameter and 340 mm length in the longitudinal direction was dipped into and then pulled up from the coating tank and dried to form an intermediate layer of 1.0 μm thickness on the conductive substrate.

Then, 2 parts by weight of oxotitanium phthalocyanine. (in which $R^7$, $R^8$, $R^9$ and $R^{10}$ each represent a hydrogen atom in the general formula (A)) having a crystal structure which shows a diffraction peak at least at a Bragg's angle 2θ (error: 2θ=0.2°) of 27.2° in the X-ray diffraction spectrum to Cu—Kα characteristic X-ray (wavelength: 1.54 Å), 1 part by weight of a polyvinyl butyral resin (Esrex BM-S: manufactured by Sekisui Chemical Industry Co.) and 97 parts by weight of methyl ethyl ketone were mixed and dispersed by a paint shaker to prepare a coating solution for use in charge generating layer. The coating solution for use in charge generating layer was coated on an intermediate layer by the same dip coating method as for the previously formed intermediate layer, and dried to form a charge generating layer of 0.4 μm thickness.

Then, 10 parts by weight of the hydrazone compound of Exemplified Compound No. 1 shown in Table 1 as the charge transporting substance, 20 parts by weight of a polycarbonate resin as binder resin (Upiron Z200: manufactured by Mitsubishi Engineering Plastics Co.), 1 part by weight of 2,6-di-t-butyl-4-methylphenol, and 0.004 parts by weight of dimethyl polysiloxane (KF-96: manufactured by Shinetsu Chemical Industry Co.) were dissolved in 110 parts by weight of THF, to prepare a coating solution for use in charge transporting layer. After coating the coating solution for use in charge transporting layer on the previously formed charge generating layer by the same dipping coating method as for the previously formed intermediate layer, it was dried at a temperature of 110° C. for one hour to form a charge transporting layer of 23 μm thickness.

In the manner as above, an electrophotographic photoreceptor of Example 14 was produced.

Examples 15, 16

Electrophotographic photoreceptors of Examples 15 and 16 were manufactured in the same manner as in Example 14 except for using Exemplified Compound No. 18 or 28 shown in Table 2 instead of Exemplified Compound No. 1 as a charge transporting substance.

Comparative Example 7

An electrophotographic photoreceptor of Comparative Example 7 was manufactured in the same manner as in Example 14 except for using Comparative Compound A represented by the structural formula (18) instead of Exemplified Compound No. 1 as a charge transporting substance.

Example 17

An electrophotographic photoreceptor of Example 17 was manufactured in the same manner as in Example 15 except for changing the amount of the polycarbonate resin as the binder resin to 25 parts by weight in forming the charge transporting layer.

Examples 18, 19

Electrophotographic photoreceptors of Examples 18 and 19 were manufactured by the same manner as in Example 14 except for changing the amount of the polycarbonate resin as a binder resin to 25 parts by weight and using Exemplified Compound No. 43 or 53 shown in Table 1 and Table 4 instead of Exemplified Compound No. 1 as a charge transporting substance in forming the charge transporting layer.

Example 20

An electrophotographic photoreceptor of Example 20 was manufactured in the same manner as in Example 14 except for changing the amount of the polycarbonate resin as the binder resin to 10 parts by weight in forming the charge transporting layer.

Reference Example

An electrophotographic photoreceptor was manufactured in the same manner as in Example 14 except for changing the amount of the polycarbonate resin as the binder resin to 31 parts by weight in forming the charge transporting layer. However, since the polycarbonate resin was not dissolved completely to increase the viscosity of the coating solution for use in charge transporting layer with THF in the same amount as that in Example 14, THF was added to prepare a coating solution for use in charge transporting layer in which the polycarbonate resin was dissolved completely and a charge transporting layer was formed by using the same.

However, the cylindrical photoreceptor was whitened and cloudy at the ends in the longitudinal direction thereof owing to the brushing phenomenon therearound, and it could not be tested for the properties thereof according to the process of Evaluation 3 mentioned below. The brushing phenomenon would have occurred owing to the excess solvent in the charge transporting layer-forming coating liquid.

[Evaluation 3]

Each of the photoreceptors of Examples 14 to 20 and Comparative Example 7 manufactured as described above was mounted to a testing copying machine modified from a commercially available digital copying machine AR-C150 (trade name of products, manufactured by Sharp Corp.) such that the circumferential rotational speed of the photoreceptor was 117 mm on every sec respectively, and the printing resistance, the electrical characteristics and the circumstantial stability of each photoreceptor were evaluated as described below. The digital copying machine AR-C150 is a negatively charged type image forming apparatus of conducting the electrophotographic process by negatively charging the surface of the photoreceptor.

(a) Printing Resistance

After forming test images of a predetermined pattern to 40,000 sheets of recording paper by using the testing copying machine, the mounted photoreceptor was taken out, and thickness d1 of the photosensitive layer of the photoreceptor taken out was measured to determine the difference between the value (d1) and the thickness d0 of the photosensitive layer before the test use as a film reduction amount Δd (=d0−d1), which was used as the evaluation index for the printing resistance. Measurement of the film thickness was conducted by an instantaneous multi-light measuring system MCPD-1100 (manufactured by Otsuka Denshi Co.) by a light interference method.

(b) Electric Characteristics and Circumstantial Stability

A surface potential meter (CATE751, manufactured by Gentec Co.) was provided inside the copying machine so as to measure the surface potential of the photoreceptor in the process of image forming. Using the copying machine, the surface potential of the photoreceptor after the charging operation by the charger was measured as the charge potential V1 (V) under a normal temperature/normal humidity (N/N) circumstance at a temperature of 22° C. and a relative humidity of 65%. Further, the surface potential of the photoreceptor after applying the laser light exposure was measured as a residual potential VL (V), which was determined as an exposure potential $VL_N$ under the N/N circumstance. It was evaluated that the chargeability was more excellent as the absolute value of the charging potential V1 was larger and the light responsiveness was evaluated to be more excellent as the absolute value of the residual potential $VL_N$ was smaller.

Further, the residual potential VL (V) was measured under the low temperature/low humidity (L/L) circumstance at a temperature of 5° C. and at a relative humidity of 20% in the same manner as under the N/N circumstance, which was determined as the residual potential $VL_L$ under the L/L circumstance. The absolute value of the difference between the residual potential $VL_N$ under the N/N circumstance and the residual potential $VL_L$ under the L/L circumstance was determined as potential fluctuation ΔVL ($=|VL_L-VL_N|$). It was judged that as the potential fluctuation ΔVL was smaller, the circumstantial stability was more excellent.

Table 11 shows the results for the evaluation.

TABLE 11

| | Charge Transporting Substance | Binder Resin/ Charge Transporting Substance | Layer Thickness Reduction Δd (μm) | N/N-Potential Characteristics | | L/L-Potential Change |
|---|---|---|---|---|---|---|
| | | | | V1 (V) | $VL_N$ (V) | ΔVL (V) |
| Example 14 | Compound No. 1 | 2.0 | 3.6 | −551 | −50 | 30 |
| Example 15 | Compound No. 18 | 2.0 | 3.7 | −548 | −44 | 32 |
| Example 16 | Compound No. 28 | 2.0 | 3.8 | −543 | −41 | 38 |
| Comparative Example 7 | Comparative Compound A | 2.0 | 4.5 | −535 | −110 | 80 |
| Example 17 | Compound No. 1 | 2.5 | 2.9 | −528 | −52 | 38 |
| Example 18 | Compound No. 43 | 2.5 | 2.9 | −533 | −50 | 40 |
| Example 19 | Compound No. 53 | 2.5 | 2.7 | −528 | −52 | 41 |
| Example 20 | Compound No. 1 | 1.0 | 11.5 | −537 | −28 | 18 |
| Reference Example | Compound No. 1 | 3.1 | — | — | — | — |

Comparing Examples 14 to 19 with Comparative Example 7 confirms that the photoreceptors of Examples 14 to 19 where the hydrazone compound of formula (1) of the invention was used as the charge transporting substance have a smaller absolute value of the exposure potential $VL_N$ in the N/N condition, as compared with the photoreceptor of Comparative Example 7 where the comparative compound A was used as the charge transporting substance. From this, it is understood that the photoreceptors of Examples 14 to 19 have good light responsibility even though the ratio of the weight of the binder resin to the weight of the charge transporting substance in the charge transporting layer (binder resin/charge transporting substance) is not less than 1.2. In addition, it is also understood that the photoreceptors of Examples 14 to 19 have a smaller potential change, $\Delta VL$ and therefore have good environment stability and have satisfactory light responsibility even in the L/L condition as compared with the photoreceptor of Comparative Example 7.

Comparing Examples 14 to 19 with Example 20 confirms that the photoreceptors of Examples 14 to 19 in which the ratio of the weight (B) of the binder resin to the weight (A) of the hydrazone compound of formula (1) of the invention, B/A is within a range of from 1.2 to 3.0 have a smaller layer thickness reduction $\Delta d$ and therefore have better printing durability, as compared with the photoreceptor of Example 20 where the ratio B/A is smaller than 1.2.

As in the above, it is understood that the hydrazone compounds of formula (1) of the invention have excellent charge transporting capability. In addition, using the hydrazone compound of the invention as a charge transporting substance has allowed provide an electrophotographic photoreceptor having good chargeability, sensitivity and light responsibility, having good electric and mechanical durability and having good environment stability.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A hydrazone compound of a general formula (1):

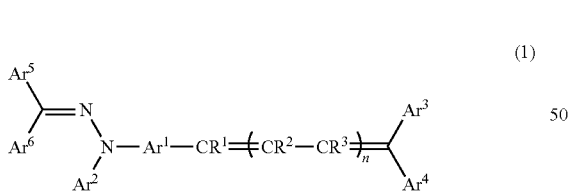

(1)

wherein $Ar^1$ represents an arylene group optionally having a substituent; $Ar^2$ represents an aryl, heterocyclic, aralkyl or alkyl group optionally having a substituent; $Ar^3$ represents an aryl, heterocyclic, aralkyl or thienylalkyl group optionally having a substituent; $Ar^4$ represents a hydrogen atom, or an aryl, heterocyclic, aralkyl or alkyl group optionally having a substituent; $Ar^5$ represents an aryl or heterocyclic group optionally having a substituent; $Ar^6$ represents a hydrogen atom, or an aryl, heterocyclic, aralkyl or alkyl group optionally having a substituent; with the proviso that, to the carbon atom to which the group $=CAr^3Ar^4$ bonds, a divalent aromatic or heterocyclic group may bond in place of the group $=CAr^3Ar^4$ bonds; to the nitrogen atom to which $=CAr^5Ar^6$ bonds, a divalent aromatic or heterocyclic group may bond in place of the group $=CAr^5Ar^6$ bonds; $R^1$, $R^2$ and $R^3$ may be the same or different, each representing a hydrogen atom, or an alkyl, aryl, heterocyclic or aralkyl group optionally having a substituent; n indicates 2; two $R^2$s and two $R^3$s each may be the same or different;

wherein the optional substituent of $Ar^5$ being selected from the group consisting of a halogen atom, a perfluoroalkyl croup, an alkyl croup, an alkoxy croup, a mono- or difluoroalkyl croup and a dialkylamino group.

2. A hydrazone compound of a general formula (1):

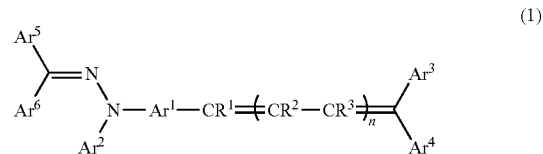

(1)

wherein $Ar^1$ represents an arylene group optionally having a substituent; $Ar^2$ represents an aryl, heterocyclic, aralkyl or alkyl group optionally having a substituent; $Ar^3$ represents an aryl, heterocyclic, aralkyl or thienylalkyl group optionally having a substituent; $Ar^4$ represents a hydrogen atom, or an aryl, heterocyclic, aralkyl or alkyl group optionally having a substituent; $Ar^5$ represents an aryl or heterocyclic group optionally having a substituent; $Ar^6$ represents an aryl, heterocyclic, aralkyl or alkyl group optionally having a substituent; with the proviso that, to the carbon atom to which the group $=CAr^3Ar^4$ bonds, a divalent aromatic or heterocyclic group may bond in place of the group $=CAr^3Ar^4$ bonds; to the nitrogen atom to which $=CAr^5Ar^6$ bonds, a divalent aromatic or heterocyclic group may bond in place of the group $=CAr^5 Ar^6$ bonds; $R^1$, $R^2$ and $R^3$ may be the same or different, each representing a hydrogen atom, or an alkyl, aryl, heterocyclic or aralkyl group optionally having a substituent; n indicates 1 or 2; when n is 2, then two $R^2$s and two $R^3$s each may be the same or different.

3. A hydrazone compound of a general formula (2):

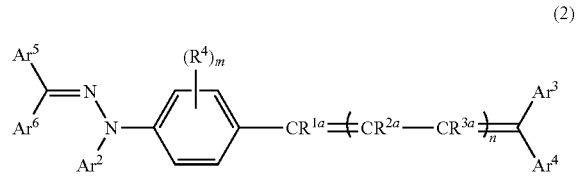

(2)

wherein $Ar^2$ represents an aryl, heterocyclic, aralkyl or alkyl group optionally having a substituent; $Ar^3$ represents an aryl, heterocyclic, aralkyl or thienylalkyl group optionally having a substituent; $Ar^4$ represents a hydrogen atom, or an aryl, heterocyclic, aralkyl or alkyl group optionally having a substituent; $Ar^5$ represents a substituted aryl group or a heterocyclic group optionally having a substituent; $Ar^6$ represents a hydrogen atom, or an aryl, heterocyclic, aralkyl or alkyl group optionally having a substituent; with the proviso that, to the carbon atom to which the group $=CAr^3Ar^4$ bonds, a divalent aromatic or heterocyclic group may bond in place of the group $=CAr^3Ar^4$ bonds; to the nitrogen atom to which $=CAr^5Ar^6$ bonds, a divalent aromatic or heterocyclic group may bond in place of the group $=CAr^5Ar^6$ bonds, n indicates 1 or 2; when n is 2, then two $R^2$s and two $R^3$s each may be the same or different;

$R^{1a}$ represents a hydrogen atom, or a C1-3 alkyl or aryl group optionally having a substituent; one of $R^{2a}$ and $R^{3a}$ is a hydrogen atom, and the other is a hydrogen atom, or a C1-3 alkyl, heterocyclic or aralkyl group optionally having a substituent, provided that, when n is 2, then two $R^{2a}$s and two $R^{3a}$s each may be the same or different; $R^4$ represents a hydrogen atom, a halogen atom, a C1-5 perfluoroalkyl group, or a C1-3 alkyl, C1-3 alkoxy, C1-5 fluoroalkyl or C2-8 dialkylamino group optionally having a substituent; m indicates an integer of from 1 to 4, provided that when m is 2 or more, then plural $R^4$s may be the same or different, $Ar^5$ is an aryl group having one or more substituents selected from a halogen atom, an alkyl group, an alkoxy group, a perhalogenoalkyl group, a halogenoalkyl group, a dialkylamino group, a styryl group and a phenylthio group, or a monocyclic or condensed-cyclic heterocyclic group optionally having an alkyl group as the substituent thereof and containing one or more hetero atoms selected from oxygen, nitrogen and sulfur atoms.

4. The hydrazone compound of a general formula (3):

(3)

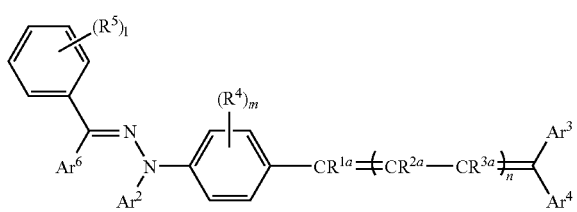

wherein $Ar^2$ represents an aryl, heterocyclic, aralkyl or alkyl group optionally having a substituent; $Ar^3$ represents an aryl, heterocyclic, aralkyl or thienylalkyl group optionally having a substituent; $Ar^4$ represents a hydrogen atom, or an aryl, heterocyclic, aralkyl or alkyl group optionally having a substituent;

$Ar^6$ represents a hydrogen atom, or an aryl, heterocyclic, aralkyl or alkyl group optionally having a substituent; with the proviso that, to the carbon atom to which the group $=CAr^3Ar^4$ bonds, a divalent aromatic or heterocyclic group may bond in place of the group $=CAr^3Ar^4$ bonds;

n indicates 1 or 2;

$R^{1a}$ represents a hydrogen atom, or a C1-3 alkyl or aryl group optionally having a substituent; one of $R^{2a}$ and $R^{3a}$ is a hydrogen atom, and the other is a hydrogen atom, or a C1-3 alkyl, heterocyclic or aralkyl group optionally having a substituent, provided that, when n is 2, then two $R^{2a}$s and two $R^{3a}$s each may be the same or different; $R^4$ represents a hydrogen atom, a halogen atom, a C1-5 perfluoroalkyl group, or a C1-3 alkyl, C1-3 alkoxy, C1-5 fluoroalkyl or C2-8 dialkylamino group optionally having a substituent; m indicates an integer of from 1 to 4, provided that when m is 2 or more, then plural $R^4$s may be the same or different, $R^5$ represents a halogen atom, a C1-3 alkyl group, a C1-3 alkoxy group, a C1-5 perfluoroalkyl group, a C1-5 fluoroalkyl group, or a C2-8 dialkylamino group; l indicates an integer of from 1 to 5, provided that when l is 2 or more, then plural $R^5$s may be the same or different; and the phenyl group to which $R^5$ bonds, and $Ar^6$ may form a condensed ring along with the carbon atoms to which they bond.

5. The hydrazone compound of claim 1 or claim 2, wherein the hydrazone compound is one represented by the following general formula (2):

(2)

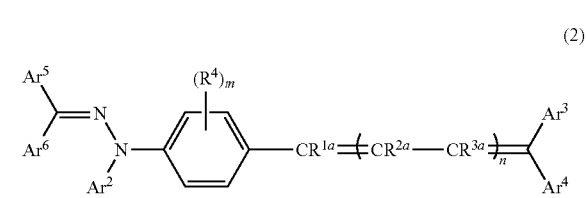

wherein $Ar^2$, $Ar^3$, $Ar^4$, $Ar^5$, $Ar^6$ and n have the same meanings as in formula (1); $R^{1a}$ represents a hydrogen atom, or a C1-3 alkyl or aryl group optionally having a substituent; one of $R^{2a}$ and $R^{3a}$ is a hydrogen atom, and the other is a hydrogen atom, or a C1-3 alkyl, heterocyclic or aralkyl group optionally having a substituent, provided that, when n is 2, then two $R^{2a}$s and two $R^{3a}$s each may be the same or different; $R^4$ represents a hydrogen atom, a halogen atom, a C1-5 perfluoroalkyl group, or a C1-3 alkyl, C1-3 alkoxy, C1-5 fluoroalkyl or C2-8 dialkylamino group optionally having a substituent; m indicates an integer of from 1 to 4, provided that when m is 2 or more, then plural $R^4$s may be the same or different.

6. The hydrazone compound claim 5, wherein in formula (2), $Ar^5$ is an aryl group optionally having one or more substituents selected from a halogen atom, an alkyl group, an alkoxy group, a perhalogenoalkyl group, a halogenoalkyl group, a dialkylamino group, a styryl group and a phenylthio group, or a monocyclic or condensed-cyclic heterocyclic group optionally having an alkyl group as the substituent thereof and containing one or more hetero atoms selected from oxygen, nitrogen and sulfur atoms.

7. The hydrazone compound of claim 5, wherein the hydrazone compound is one represented by the following general formula (3):

(3)

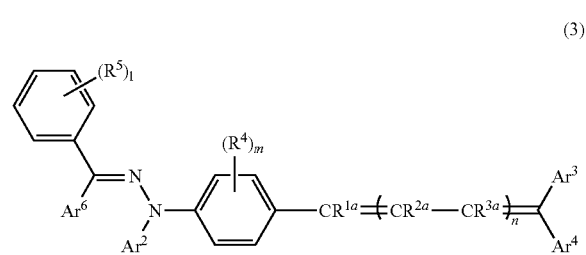

wherein $Ar^2$, $Ar^3$, $Ar^4$, $Ar^6$ and n have the same meanings as in formula (1); $R^{1a}$, $R^{2a}$, $R^{3a}$, $R^4$ and m have the same meanings as in formula (2); $R^5$ represents a hydrogen atom, a halogen atom, a C1-3 alkyl group, a C1-3 alkoxy group, a C1-5 perfluoroalkyl group, a C1-5 fluoroalkyl group, or a C2-8 dialkylamino group; l indicates an integer of from 1 to 5, provided that when l is 2 or more, then plural $R^5$s may be the same or different; and the phenyl group to which $R^5$ bonds, and $Ar^6$ may form a condensed ring along with the carbon atoms to which they bond.

8. The hydrazone compound of claim 7, wherein in formula (3), $R^5$ is a hydrogen atom, a C1-3 alkyl group, or a C1-3 alkoxy group.

9. The hydrazone compound of claim 7, wherein in formula (3), $Ar^2$ is a C1-3 alkyl group, a phenyl group optionally having a halogen atom, a C1-3 alkyl group or a phenylthio group as the substituent thereof, a benzyl group optionally having a C1-3 alkoxy group as the substituent thereof, or a monocyclic or condensed-cyclic heterocyclic group optionally having a C1-3 alkyl group as the substituent thereof and having one or two hetero atoms selected from sulfur and nitrogen atoms;

Ar$^3$ is a phenyl group optionally having a C1-3 alkyl group, a C1-3 alkoxy group or a C1-3 halogenoalkyl group as the substituent thereof, an aralkyl group where the alkyl moiety has from 1 to 2 carbon atoms, a thienylalkyl group where the alkyl moiety has from 1 to 3 carbon atoms, or a monocyclic or condensed-cyclic heterocyclic group optionally having a C1-3 alkyl group as the substituent thereof and having one or more hetero atoms selected from oxygen, sulfur and nitrogen atoms;

Ar$^4$ is a hydrogen atom, a C1-3 alkyl group, or a phenyl group optionally having a C1-3 alkyl group, a C1-3 alkoxy group or a dialkylamino group where the alkyl moiety has from 1 to 3 carbon atoms, as the substituent thereof;

Ar$^6$ is a hydrogen atom, a C1-3 alkyl group, or a monocyclic heterocyclic group containing an oxygen atom as the hetero atom therein;

R$^{1a}$ is a hydrogen atom, a C1-3 alkyl group, or a phenyl group;

one of R$^{2a}$ and R$^{3a}$ is a hydrogen atom, and the other is a hydrogen atom, a C1-3 alkyl group, a benzyl group, or a monocyclic heterocyclic group containing a sulfur atom as the hetero atom therein; and R$^4$ is a hydrogen atom, or a C1-3 alkyl group.

10. The hydrazone compound of claim 7, wherein in formula (3), R$^{1a}$, R$^{2a}$ and R$^{3a}$ are all hydrogen atoms.

11. The hydrazone compound of claim 4 wherein in formula (3), R$^5$ is a C1-3 alkyl group, or a C1-3 alkoxy group.

12. The hydrazone compound of claim 4, wherein in formula (3), Ar$^2$ is a C1-3 alkyl group, a phenyl group optionally having a halogen atom, a C1-3 alkyl group or a phenylthio group as the substituent thereof, a benzyl group optionally having a C1-3 alkoxy group as the substituent thereof, or a monocyclic or condensed-cyclic heterocyclic group optionally having a C1-3 alkyl group as the substituent thereof and having one or two hetero atoms selected from sulfur and nitrogen atoms;

Ar$^3$ is a phenyl group optionally having a C1-3 alkyl group, a C1-3 alkoxy group or a C1-3 halogenoalkyl group as the substituent thereof, an aralkyl group where the alkyl moiety has from 1 to 2 carbon atoms, a thienylalkyl group where the alkyl moiety has from 1 to 3 carbon atoms, or a monocyclic or condensed-cyclic heterocyclic group optionally having a C1-3 alkyl group as the substituent thereof and having one or more hetero atoms selected from oxygen, sulfur and nitrogen atoms;

Ar$^4$ is a hydrogen atom, a C1-3 alkyl group, or a phenyl group optionally having a C1-3 alkyl group, a C1-3 alkoxy group or a dialkylamino group where the alkyl moiety has from 1 to 3 carbon atoms, as the substituent thereof;

Ar$^6$ is a hydrogen atom, a C1-3 alkyl group, or a monocyclic heterocyclic group containing an oxygen atom as the hetero atom therein;

R$^{1a}$ is a hydrogen atom, a C1-3 alkyl group, or a phenyl group;

one of R$^{2a}$ and R$^{3a}$ is a hydrogen atom, and the other is a hydrogen atom, a C1-3 alkyl group, a benzyl group, or a monocyclic heterocyclic group containing a sulfur atom as the hetero atom therein; and R$^4$ is a hydrogen atom, or a C1-3 alkyl group.

13. The hydrazone compound of claim 4, wherein in formula (3), R$^{1a}$, R$^{2a}$ and R$^{3a}$ are all hydrogen atoms.

14. An electrophotographic photoreceptor comprising:
a conductive substrate; and
a photosensitive layer provided on the conductive substrate,
wherein the photosensitive layer contains the hydrazone compound of claim 1 or claim 2 or claim 3 or claim 4.

15. The electrophotographic photoreceptor of claim 14, wherein the photosensitive layer further contains an oxotitanium phthalocyanine compound.

16. The electrophotographic photoreceptor of claim 15, wherein the oxotitanium phthalocyanine compound has a crystal structure that shows a diffraction peak at least at a Bragg angle 2θ (error: 2θ±0.2°) of 27.2° in the X-ray diffraction spectrum thereof to a Cu—Kα characteristic X ray (wavelength: 1.54 angstroms).

17. The electrophotographic photoreceptor of claim 14, wherein the photosensitive layer comprises a charge generating layer containing a charge generating substance and a charge transporting layer containing a charge transporting substance, and
the charge transporting substance contains the hydrazone compound.

18. The electrophotographic photoreceptor of claim 17, wherein the charge transporting layer further contains a binder resin, and
the ratio of the weight (B) of the binder resin to the weight (A) of the hydrazone compound in the charge transporting layer, (B/A) is from 1.2 to 3.0.

19. The electrophotographic photoreceptor of claim 14, further comprising an intermediate layer provided between the conductive substrate and the photosensitive layer.

20. An image forming apparatus, comprising:
the electrophotographic photoreceptor of claim 14;
charging means for charging the electrophotographic photoreceptor;
exposing means for exposing the charged electrophotographic photoreceptor to light; and
developing means for developing the electrostatic latent image formed through exposure.

21. An electrophotographic photoreceptor comprising:
a conductive substrate; and
a photosensitive layer provided on the conductive substrate,
wherein the photosensitive layer contains the hydrazone compound of claim 1 or claim 2 or claim 3 or claim 4.

22. The electrophotographic photoreceptor of claim 21, wherein the photosensitive layer further contains an oxotitanium phthalocyanine compound.

23. The electrophotographic photoreceptor of claim 22, wherein the oxotitanium phthalocyanine compound has a crystal structure that shows a diffraction peak at least at a Bragg angle 2θ (error: 2θ±0.2°) of 27.2° in the X-ray diffraction spectrum thereof to a Cu—Kα characteristic X ray (wavelength: 1.54 angstroms).

24. The electrophotographic photoreceptor of claim 21, wherein the photosensitive layer comprises a charge generating layer containing a charge generating substance and a charge transporting layer containing a charge transporting substance, and
the charge transporting substance contains the hydrazone compound.

25. The electrophotographic photoreceptor of claim 24, wherein the charge transporting layer further contains a binder resin, and the ratio of the weight (B) of the binder resin to the weight (A) of the hydrazone compound in the charge transporting layer, (B/A) is from 1.2 to 3.0.

26. The electrophotographic photoreceptor of claim 21, further comprising an intermediate layer provided between the conductive substrate and the photosensitive layer.

27. An image forming apparatus, comprising:

the electrophotographic photoreceptor of claim 21;

charging means for charging the electrophotographic photoreceptor;

exposing means for exposing the charged electrophotographic photoreceptor to light; and developing means for developing the electrostatic latent image formed through exposure.

* * * * *